United States Patent
Kornacker et al.

(10) Patent No.: US 7,314,726 B2
(45) Date of Patent: Jan. 1, 2008

(54) BETA SECRETASE EXOSITE BINDING PEPTIDES AND METHODS FOR IDENTIFYING BETA SECRETASE MODULATORS

(75) Inventors: Michael G. Kornacker, Princeton, NJ (US); Robert A. Copeland, Hockessin, DE (US); Joseph Hendrick, Portland, CT (US); Zhihong Lai, West Chester, PA (US); Claudio Mapelli, Plainsboro, NJ (US); Mark Richard Witmer, Pennington, NJ (US); Jovita Marcinkeviciene, Washington Crossing, PA (US); William Metzler, Doylestown, PA (US); Ving Lee, Hamilton, NJ (US); Douglas James Riexinger, Flemington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 590 days.

(21) Appl. No.: 10/685,898

(22) Filed: Oct. 15, 2003

(65) Prior Publication Data
US 2004/0121412 A1 Jun. 24, 2004

Related U.S. Application Data

(60) Provisional application No. 60/418,679, filed on Oct. 15, 2002.

(51) Int. Cl.
*G01N 33/53* (2006.01)
(52) U.S. Cl. .................. 435/7.5; 435/7.1; 435/7.71; 435/7.8
(58) Field of Classification Search .............. None
See application file for complete search history.

(56) References Cited

U.S. PATENT DOCUMENTS 5,962,407 A 10/1999 Kelly 6,420,534 B1 7/2002 Gurney et al.
6,440,698 B1 8/2002 Gurney et al.
2002/0055459 A1* 5/2002 Chopra et al. .................. 514/1

OTHER PUBLICATIONS

Mullan, et al., "A pathogenic mutation for probable Alzheimer's disease in the APP gene at the N-terminus of β-amyloid", Nature Genetics, vol. 1, pp. 345-347 (1992).
Marcinkeviciene, et al., "Mechanism of Inhibition of β-Site Amyloid Precursor Protein-cleaving Enzyme (BACE) by a Statine-based Peptide", J. of Biolog. Chem., vol. 276, No. 26., pp. 23790-23794.
Mallender, et al., "Characterization of Recombinant, Soluble β-Secretase from an Insect Cell Expression System", Molecular Pharmacology, vol. 59, No. 3, pp. 619-626 (2001).
Vassar, et al., "β-Secretase Cleavage of Alzheimer's Amyloid Precursor Protein by the Transmembrane Aspartic Protease BACE," Science, vol. 286, pp. 735-741 (1999).
Sidhu, et al., "Phage Display for Selection of Novel Binding Peptides", Methods in Enzymology, vol. 328, pp. 333-363 (2000).
Haniu, et al., "Characterization of Alzheimer's β-Secretase Protein BACE", J. of Biol. Chem., vol. 275, No. 28, pp. 21099-21106 (2000).
Gruninger-Leitch, et al., "Substrate and Inhibitor Profile of BACE (β-Secretase) and Comparison with Other Mammalian Aspartic Proteases", J. Biol. Chem., vol. 277(7), pp. 4687-4693 (2002).

* cited by examiner

*Primary Examiner*—Lorraine Spector
*Assistant Examiner*—Gregory S. Emch
(74) *Attorney, Agent, or Firm*—Melissa Handler; John A. Lamerdin

(57) ABSTRACT

The present invention provides peptides that specifically bind to BACE at a newly discovered exosite. The invention also provides methods for identifying peptides that bind to a BACE exosite. The invention further provides methods for identifying compounds that bind to a BACE exosite and modulate BACE activity. In another aspect, the invention provides methods for treating or preventing neurodegenerative disorders such as Alzheimer's disease by administering compounds that bind to a BACE exosite and modulate BACE activity.

3 Claims, 15 Drawing Sheets

Molecule X

Molecule Yn (n=1-4)

Molecule Z

BETA SECRETASE EXOSITE BINDING PEPTIDES AND METHODS FOR IDENTIFYING BETA SECRETASE MODULATORS

The present patent application claims the benefit of U.S. Provisional Patent Application Ser. No. 60/418,679, filed Oct. 15, 2002, the disclosure of which is incorporated herein by reference in its entirety.

FIELD OF THE INVENTION

The present invention relates to peptides that bind to beta secretase ("β-secretase") at a newly discovered exosite within the catalytic domain of the enzyme, and use of these peptides and variants thereof to identify therapeutic molecules useful for the treatment of neurological disorders.

BACKGROUND OF THE INVENTION

Alzheimer's disease ("AD") is a devastating neurodegenerative disease that affects millions of elderly patients worldwide. AD is characterized clinically by progressive loss of memory, orientation, cognitive function, judgement and emotional stability. With increasing age, the risk of developing AD increases exponentially, so that by age 85 some 20-40% of the population is affected. Memory and cognitive function deteriorate rapidly within the first 5 years after diagnosis of mild to moderate impairment, and death due to disease complications is an inevitable outcome. AD is the most common cause of nursing home admittance in the United States; hence, in addition to the morbidity and mortality experienced by the patient, there are considerable economic and emotional burdens placed on the family, caregivers and society at large. The only recognized treatment currently available for AD is acetylcholinesterase inhibitors, which merely treat the symptoms of cognitive impairment. No method for prevention or treatment of the pathophysiology of AD is currently available.

Diagnosis of AD is based mainly on subjective assessments of memory and cognitive function. Definitive diagnosis can only be made post-mortem, based on histopathological examination of brain tissue from the patient. Two histological hallmarks of AD are the occurrence of neurofibrillar tangles of hyperphosphorylated tau protein and of proteinaceous amyloid plaques, both within the cerebral cortex of AD patients. The amyloid plaques are composed mainly of a peptide of 39 to 42 amino acids designated beta-amyloid, also referred to as β-amyloid, amyloid beta, Aβ, βAP, β/A4; and referred to herein as beta-amyloid and Aβ. It is now clear that the Aβ peptide is derived from a type 1 integral membrane protein, termed beta amyloid precursor protein (also referred to as "β-APP" and "APP") through two sequential proteolytic events. First, the APP is hydrolyzed at a site N-terminal of the transmembrane alpha helix by a specific proteolytic enzyme referred to as β-secretase. The soluble N-terminal product of this cleavage event diffuses away from the membrane, leaving behind the membrane-associate C-terminal cleavage product, referred to as C99. The protein C99 is then further hydrolyzed within the transmembrane alpha helix by a specific proteolytic enzyme referred to as γ-secretase. This second cleavage event liberates the Aβ peptide and leaves a membrane-associated "stub". The Aβ peptide thus generated is secreted from the cell into the extracellular matrix where it eventually forms the amyloid plaques associated with AD.

Several lines of evidence suggest that abnormal accumulation of Aβ plays a key role in the pathogenesis of AD. First, Aβ is the major protein component of amyloid plaques. Second, Aβ is neurotoxic and may be causally linked to the neuronal death associated with AD. Third, missense DNA mutations at several positions within the APP protein can be found in affected members but not unaffected members of several families with a genetically determined (familial) form of AD. For example, one familial form of AD is linked to a pair of mutations, referred to as the "Swedish mutations", that are immediately proximal to the site of β-secretase-mediated hydrolysis of APP (Mullan et al., (1992) *Nature Genet.* 1:345-347). Patients bearing the Swedish mutant form of APP develop AD at a much earlier age (typically within the fourth decade of life) and likewise progress to severe dementia at a much earlier age. Histopathological examination of the brains of patients suffering from the "Swedish mutant" form of familial AD is identical to that of brains from patients suffering from non-familial, sporadic forms of the disease. It is therefore hypothesized that halting the production of Aβ will prevent and/or reduce the neurodegeneration and other pathologies of AD. One method of halting Aβ production would be to administer specific inhibitors of one or both of the proteolytic enzymes involved in APP processing, namely, β-secretase and γ-secretase. The molecular identity of the protein responsible for γ-secretase activity has not yet been determined, although there is a preponderance of data suggesting a role for the proteins presenilin-1 and presenilin-2 in this enzymatic action. Nevertheless, compounds that inhibit the action of γ-secretase, and thus inhibit Aβ production in cell culture have been identified by several groups.

Recently the molecular identity of the protein responsible for β-secretase activity has been determined and this protein is commonly referred to as BACE (for Beta-site APP Cleaving Enzyme). This enzyme is a type 1 membrane protein that folds into an extra-membranous globular catalytic domain that is tethered to the membrane by a single alpha helix. The catalytic domain of BACE contains the canonical signature motifs for an aspartyl protease, and the enzymatic activity of recombinant versions of the catalytic domain of human BACE is consistent with this designation. It is well known that aspartyl proteases can be effectively inhibited by small molecules and peptides that bind to, and hence block, the site on the enzyme molecule at which the chemical transformations of the substrate molecule takes place. This site of chemical reactivity is commonly referred to as the enzyme active site. For aspartyl proteases this site contains the two chemically reactive aspartic acid residues from which this class of enzymes derive its name. During the course of enzymatic action on the substrate molecule, the enzyme goes through an intermediate state in which the carbonyl carbon of the hydrolyzable amide bond of the substrate forms four coordinate bonds, engaging the active site aspartic acid residues of the enzyme.

A common strategy for inhibiting aspartyl proteases is to prepare a small peptide of amino acid composition similar to the substrate molecule but replacing the hydrolyzable amide bond with a chemical group that mimics the four coordinate carbon intermediate species just described. It is well known that chemical groups such as statines, hydroxyethylenes, hydroxyethylamines and similar structures are very effective for this purpose. Indeed, peptidic inhibitors of BACE, incorporating statine and hydroxyethylene structures have been reported. Recently the 3-dimensional structure of the catalytic domain of human BACE in complex with a hydroxyethylene-based peptidic inhibitor referred to as OM99-2 has been solved by the methods of x-ray crystallography. The resulting structure confirmed that the inhibitor binds within the enzyme active site, engaging the active site aspartic acid residues as expected. Hence, active site-directed inhibitors of BACE can be designed and may prove useful as pharmacological agents for the treatment of AD. Historically, however, it has proved difficult to develop molecules of pharmacological utility based on active site-directed inhibitors of aspartyl proteases. While very potent inhibitors have been identified in vitro, active site-directed inhibitors of aspartyl proteases may present in vivo issues of oral bioavailability and pharmacokinetic half-life.

In addition to the active site, some proteolytic enzymes contain additional binding pockets that engage the substrate protein at locations distal to the site of chemical transformation. These binding pockets are referred to as exosites and can contribute significantly to the stabilization of the enzyme-substrate binary complex by providing important structural determinants of interaction. Additionally, exosites on some proteolytic enzymes can act as allosteric regulators of enzyme activity, so that binding interactions at the exosite are transmitted through conformational changes of the enzyme to the active site, where structural changes can augment or diminish the chemical reactivity of the active site. In some cases molecules have been identified that bind to an exosite, rather than the active site, of proteolytic enzymes and these have proved to be effective inhibitors of enzymatic action. Hence, exosites represent an alternative target for inhibitory ligand binding to proteolytic enzymes. Because the exosites are distinct from the active sites of these enzymes, the nature of the molecules that bind to the exosites can be very different from active site-directed inhibitors. In favorable cases, the nature of the molecules binding to the exosites are more pharmacologically tractable relative to the active site-directed inhibitors of the same enzyme.

SUMMARY OF THE INVENTION

The present invention provides peptides that specifically bind to BACE at a newly discovered exosite within the catalytic domain of the enzyme, and are referred to herein as "exosite binding peptides" or "EBPs". The peptides of the present invention can be used to modulate BACE activity and interfere with hydrolysis of APP and APP-derived substrates.

The invention also provides methods for identifying peptides that bind to a BACE exosite comprising contacting BACE with at least one peptide, and determining whether the peptide specifically binds to BACE at a site other than the active site of BACE.

The invention further provides methods of using the peptides and variants thereof for identifying compounds that bind to BACE exosites and modulate BACE activity. In another aspect, the invention provides methods for treating or preventing neurological disorders such as Alzheimer's disease by administering compounds that bind to a BACE exosite and inhibit beta-amyloid production.

DETAILED DESCRIPTION OF THE INVENTION

Figure 1:
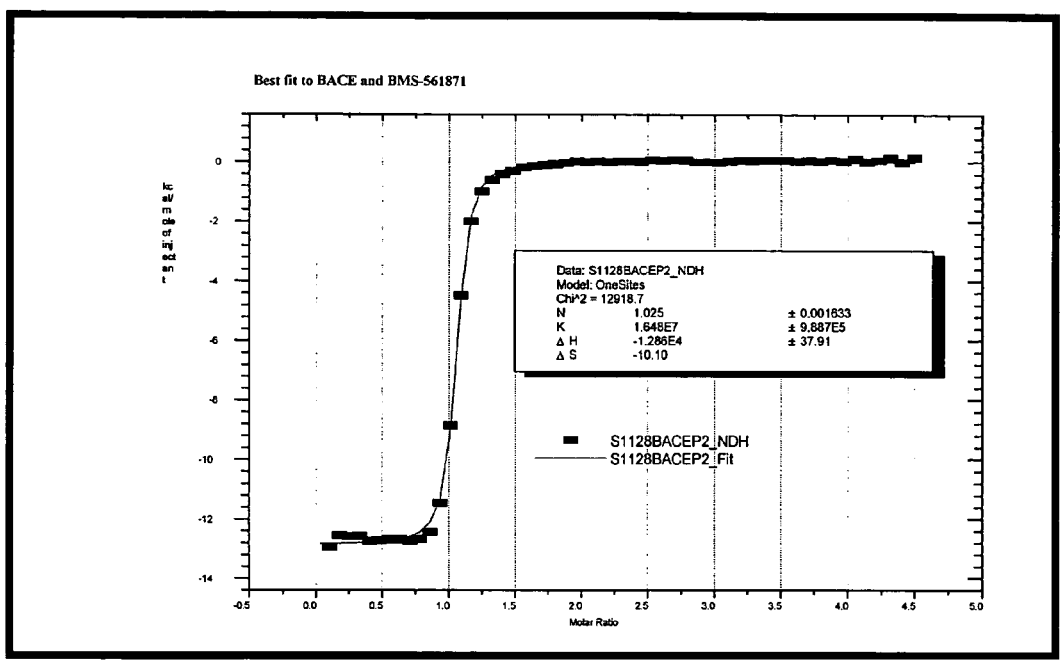
FIG. 1 shows isothermal calorimetry data quantitatively determining the binding affinity of peptide NLTTYPYFIPLP (SEQ ID NO:19) to BACE at 25° C., in Dulbecco's PBS wherein the parameters were $K_A=1.65\times10^7$ $M^{-1}$; $K_d=61$ nM; n=1.03; and $\Delta H=-12.9$ kcal/mol.

In accordance with the present invention, we have discovered peptides that specifically bind to a Beta-site APP Cleaving Enzyme (BACE) binding site that is not the BACE active site. The term "BACE exosite" as used herein refers to a BACE binding site that is not the BACE active site. A BACE exosite is an important target site for modulating the processing of APP and the production of Aβ.

The present invention provides isolated peptides that specifically bind to BACE at an exosite and modulate BACE activity. Peptides that specifically bind to BACE at an exosite are also referred to herein as "exosite binding peptides" (EBPs). The terms "specific binding" or "specifically bind" refer to the interaction between a protein and a binding molecule, such as a compound. The interaction is dependent upon the presence of a particular structure (i.e., an enzyme binding site, an antigenic determinant or epitope) of the protein that is recognized by the binding molecule. For example, if a compound is specific for enzyme binding site "A", the presence of the compound in a reaction containing a protein including enzyme binding site A, and a labeled peptide that specifically binds to enzyme binding site A will reduce the amount of labeled peptide bound to the protein. In contrast, nonspecific binding of a compound to the protein does not result in a concentration-dependent displacement of the labeled peptide from the protein.

As used herein the term "active site" means the site on the enzyme molecule at which the chemical transformations of the substrate molecule take place. The term "exosite" as used herein means any site on the enzyme molecule other than the active site.

The present invention provides a method for identifying peptides that specifically bind to a BACE exosite comprising:

(a) contacting BACE with at least one peptide; and
(b) determining whether the peptide specifically binds to BACE at a site other than the active site of BACE.

In one embodiment, the EBPs of the present invention can be used to treat disorders such as neurodegenerative disorders. In this embodiment, the EBP is administered to a patient in a therapeutic composition with a pharmaceutically acceptable carrier. Moreover, a combination of EBPs may be administered to a patient to treat a neurodegenerative disorder, such as Alzheimer's disease.

Peptides that bind to BACE exosites can be identified by screening peptide libraries. Preferably, phage display random libraries and phage ELISA assays are used to identify the EBPs. Preparation of phage display libraries and phage ELISA assays are known to those skilled in the art, see, for example, B. K. Kay, J. Winter, J. McCafferty (eds.), *Phage Display of Peptides and Proteins. A Laboratory Manual*, Academic Press, (1996), chapters 5, 7, 13 and 16. In a preferred embodiment, the peptides of the peptide libraries are 5 mer to 30 mer peptides. The phage display library can be screened by isolating viral particles that bind to targets. The isolates can be grown up, and the displayed peptide sequence responsible for binding can be deduced by DNA sequencing.

In a preferred embodiment, the present invention provides EBPs comprising an amino acid sequence having a Tyr-Pro-Tyr-Phe (also referred to herein as "YPYF") (SEQ ID NO:1) motif wherein the EBPs are capable of specifically binding to a BACE exosite and inhibiting BACE activity.

Other preferred EBPs of the present invention include a BACE exosite binding motif comprising amino acid residues Tyr-Pro-Tyr-Phe-Ile (also referred to herein as "YPYFI") (SEQ ID NO:2). Preferred EBPs of the present invention comprise at least one of the following amino acid sequences: Xaa-Tyr-Pro-Tyr-Phe (SEQ ID NO:3), Xaa-Tyr-Pro-Tyr-Phe-Xaa (SEQ ID NO:4), Xaa-Tyr-Pro-Tyr-Phe-Xaa-Xaa (SEQ ID NO:5), Tyr-Pro-Tyr-Phe-Xaa (SEQ ID NO:6) Tyr-Pro-Tyr-Phe-Xaa-Xaa (SEQ ID NO:7), His-Tyr-Pro-Tyr-Phe (SEQ ID NO:8), Tyr-Pro-Tyr-Phe-Ile (SEQ ID NO:2), Tyr-Pro-Tyr-Phe-Ile-Pro (SEQ ID NO:9), Tyr-Pro-Tyr-Phe-Ile-Pro-Leu (SEQ ID NO:10), Tyr-Pro-Tyr-Phe-Leu-Pro-Ile (SEQ ID NO:11), Tyr-Pro-Tyr-Phe-Xaa-Pro-Ile (SEQ ID NO:12), Tyr-Pro-Tyr-Phe-Xaa-Pro-Xaa (SEQ ID NO:13), His-Tyr-Pro-Tyr-Phe-Ile-Pro (SEQ ID NO:14) Tyr-Pro-Tyr-Phe-Leu (SEQ ID NO: 15), Tyr-Pro-Tyr-Phe-Leu-Pro (SEQ ID NO:16), His-Tyr-Pro-Tyr-Phe-Leu-Pro (SEQ ID NO:17), and His-Tyr-Pro-Tyr-Phe-Ile-Pro-Leu (SEQ ID NO:18). As used herein the term "Xaa" means any amino acid, i.e., either naturally or non-naturally occurring amino acid.

The most preferred EBPs of the present invention are Asn-Leu-Thr-Thr-Tyr-Pro-Tyr-Phe-Ile-Pro-Leu-Pro (SEQ ID NO:19) also referred to herein as "NLTTYPYFIPLP" and "BMS-561871"; Ala-Leu-Tyr-Pro-Tyr-Phe-Leu-Pro-Ile-Ser-Ala-Lys (SEQ ID NO:20) also referred to herein as "ALYPYFLPISAK" and "BMS-561877"; and Tyr-Pro-Tyr-Phe-Ile-Pro-Leu (SEQ ID NO:10) also referred to herein as "YPYFIPL" and "BMS-593925."

Other preferred EBPs of the present invention comprise amino acid sequences having a WPXFI (SEQ ID NO:21) motif. Preferred EBPs having the WPXFI motif are Glu-Thr-Trp-Pro-Arg-Phe-Ile-Pro-Tyr-His-Ala-Leu-Thr-Gln-Gln-Thr-Leu-Lys-His-Gln-Gln-His-Thr (SEQ ID NO:22), Thr-Ala-Glu-Tyr-Glu-Ser-Arg-Thr-Ala-Arg-Thr-Ala-Pro-Pro-Ala-Pro-Thr-Gln-His-Trp-Pro-Phe-Phe-Ile-Arg-Ser-Thr (SEQ ID NO:23) and His-Trp-Pro-Phe-Phe-Ile-Arg-Ser (SEQ ID NO:57).

In the most preferred embodiment, the EBPs of the present invention contain from about 5 to about 30 amino acid residues.

The amino acid sequence of the subject EBPs can be modified for such purposes as enhancing therapeutic or prophylactic efficacy, or stability (e.g., ex vivo shelf life and resistance to proteolytic degradation in vivo). Such modified peptide can be produced, for instance, by amino acid substitution, deletion, or addition different codon usage. Likewise, different codons may be selected to increase the rate at which expression of the peptide/polypeptide occurs in a particular prokaryotic or eukaryotic host in accordance with the frequency with which particular codons are utilized by the host.

Variant EBPs resulting from amino acid substitutions, deletions, or additions of the EBP sequences described herein are within the scope of the present invention. Examples of such variant EBPs are EBPs wherein a leucine is replaced with an isoleucine or valine, an aspartic acid with a glutamic acid, a threonine with a serine, or a similar replacement of an amino acid with a structurally related amino acid (i.e., conservative mutations). Conservative replacements are those that take place within a family of amino acids that are related in their side chains. Genetically encoded amino acids can be divided into the following families: (1) acidic: aspartatic acid, glutamatic acid; (2) basic: lysine, arginine, histidine; (3) nonpolar: alanine, valine, leucine, isoleucine, proline, phenylalanine, methionine, tryptophan; (4) uncharged polar: glycine, asparagine, glutamine, cysteine, serine, threonine, and tyrosine; (5) aromatic: phenylalanine, tryptophan, and tyrosine; (6) aliphatic: glycine, alanine, valine, leucine, isoleucine, serine, threonine, with serine and threonine optionally being grouped separately as aliphatic-hydroxyl; and (7) amide: asparagine, glutamine; and (8) sulfur-containing: cysteine and methionine (see, for example, Stryer (ed.), *Biochemistry*, ($2^{nd}$ ed.), W H Freeman and Co. (1981)).

The EBPs of the present invention can also be peptide mimics wherein one or more of the amino acid residues is replaced with a nonnaturally occurring amino acid residue. For example, one or more amino acid residues may be tagged with a photoaffinity label such as, for example, benzophenone.

Those skilled in the art of peptide chemistry are aware that amino acid residues occur as both D and L isomers, and that the instant invention contemplates the use of either D or L isomers or a mixture of isomers of amino acid residues incorporated in the synthesis of the peptides described herein.

The EBPs of the present invention can be produced by conventional methods known to those skilled in the art. In one embodiment, the peptide may be produced by expression from a transformed host. For example, a host cell transfected with a nucleic acid vector directing expression of a nucleotide sequence encoding the EBP can be cultured under appropriate conditions to allow expression of the peptide to occur. The peptide may be secreted and isolated from a mixture of cells and medium containing the recombinant EBP. Alternatively, the peptide may be retained cytoplasmically and the cells harvested, lysed and the peptide isolated. A cell culture includes host cells, media and other byproducts. Suitable media for cell culture are well known in the art. The recombinant EBP can be isolated from cell culture medium, host cells, or both using techniques known in the art for purifying peptides including ion-exchange chromatography, reverse phase chromatography, gel filtration chromatography, ultrafiltration, electrophoresis, and immunoaffinity purification with antibodies specific for such peptides. In one embodiment of the invention, the recombinant EBP is a fusion protein containing a domain that facilitates its purification, such as EBP-GST fusion protein.

In addition, cell-free translation systems (see Sambrook et al., *Molecular Cloning: A Laboratory Manual*, ($2^{nd}$ ed.) Cold Spring Harbor Laboratory, Cold Spring Harbor, N.Y., (1989)) can be used to produce recombinant EBPs. Suitable cell-free expression systems for use in accordance with the present invention include rabbit reticulocyte lysate, wheat germ extract, canine pancreatic microsomal membranes, *E. coli* S30 extract, and coupled transcription/translation systems (Promega Corp., Madison, Wis.). These systems allow expression of recombinant polypeptides or peptides upon the addition of cloning vectors, DNA fragments, or RNA sequences containing coding regions and appropriate promoter elements.

In another embodiment, nucleic acid sequences encoding the EBPs of the present invention may be synthesized, in whole or in part, using chemical methods well known in the art (see, e.g., Caruthers, M. H. et al., (1980) *Nucl. Acids Res. Symp. Ser.* 215-223; Horn, T. et al., (1980) *Nucl. Acids Res. Symp. Ser.* 225-232). Such nucleic acid sequences can be expressed by conventional methods known to those skilled in the art. The present invention provides isolated codon-usage variants that do not alter the polypeptide sequence or biological activity of the EBPs disclosed herein. For example, a number of amino acids are designated by more than one triplet. Codons that specify the same amino acid, or synonyms may occur due to degeneracy in the genetic code. Examples include nucleotide codons CGT, CGG, CGC, and CGA encoding the amino acid, arginine (R); or codons GAT, and GAC encoding the amino acid, aspartic acid (D). Thus, a protein or peptide can be encoded by one or more nucleic acid molecules that differ in their specific nucleotide sequence, but still encode peptide or protein molecules having identical sequences. The amino acid coding sequence is as follows:

| Amino Acid | Three Letter Symbol | One Letter Symbol | Codons |
|---|---|---|---|
| Alanine | Ala | A | GCU, GCC, GCA, GCG |
| Cysteine | Cys | C | UGU, UGC |
| Aspartic Acid | Asp | D | GAU, GAC |
| Glutamic Acid | Glu | E | GAA, GAG |
| Phenylalanine | Phe | F | UUU, UUC |
| Glycine | Gly | G | GGU, GGC, GGA, GGG |
| Histidine | His | H | CAU, CAC |
| Isoleucine | Ile | I | AUU, AUC, AUA |
| Lysine | Lys | K | AAA, AAG |
| Leucine | Leu | L | UUA, UUG, CUU, CUC, CUA, CUG |
| Methionine | Met | M | AUG |
| Asparagine | Asn | N | AAU, AAC |
| Proline | Pro | P | CCU, CCC, CCA, CCG |
| Glutamine | Gln | Q | CAA, CAG |
| Arginine | Arg | R | CGU, CGC, CGA, CGG, AGA, AGG |
| Serine | Ser | S | UCU, UCC, UCA, UCG, AGU, AGC |
| Threonine | Thr | T | ACU, ACC, ACA, ACG |
| Valine | Val | V | GUU, GUC, GUA, GUG |
| Tryptophan | Trp | W | UGG |
| Tyrosine | Tyr | Y | UAU, UAC |

The codon-usage variants may be generated by recombinant DNA technology. Codons may be selected to optimize the level of production of the EBP in a particular prokaryotic or eukaryotic expression host, in accordance with the frequency of codon utilized by the host cell. Alternative reasons for altering the nucleotide sequence encoding an EBP include the production of RNA transcripts having more desirable properties, such as an extended half-life or increased stability. A multitude of variant nucleotide sequences that encode the respective EBPs may be isolated, as a result of the degeneracy of the genetic code. Accordingly, the present invention provides selecting every possible triplet codon to generate every possible combination of nucleotide sequences that encode the disclosed EBPs.

Alternatively, the peptide or protein itself may be produced using chemical methods to synthesize the amino acid sequence of the EBP, or a portion thereof. For example, peptide synthesis can be performed using various solid-phase techniques (see, e.g., Roberge, J. Y. et al., (1995) *Science* 269:202-204), cleavage from a naturally-derived, synthetic or semi-synthetic polypeptide, automated synthesis using a peptide synthesizer, or a combination of these techniques.

Solid-phase techniques that can be used to synthesize the EBPs of the present invention are described in G. Barany and R. B. Merrifield, *The Peptides: Analysis, Synthesis, Biology*; Volume 2—"Special Methods in Peptide Synthesis, Part A", pp. 3-284, (E. Gross and J. Meienhofer, eds.), Academic Press, New York, 1980; and in J. M. Stewart and J. D. Young, *Solid-Phase Peptide Synthesis*, $2^{nd}$ Ed., Pierce Chemical Co., Rockford, Ill., (1984), for example. The preferred strategy for use in this invention is based on the Fmoc (9-Fluorenylmethylmethyloxycarbonyl) group for temporary protection of the α-amino group, in combination with the tert-butyl group for temporary protection of the amino acid side chains (see for example E. Atherton and R. C. Sheppard, "The Fluorenylmethoxycarbonyl Amino Protecting Group", in *The Peptides: Analysis, Synthesis, Biology*; Volume 9—"Special Methods in Peptide Synthesis, Part C", pp. 1-38, (S. Undenfriend and J. Meienhofer, eds.), Academic Press, San Diego, (1987)).

The peptides are synthesized in a stepwise manner on an insoluble polymer support (also referred to as "resin") starting from the C-terminus of the peptide. A synthesis is begun by appending the C-terminal amino acid of the peptide to the resin through formation of an amide linkage. This allows the eventual release of the resulting peptide as a C-terminal amide. The C-terminal amino acid and all other amino acids used in the synthesis are required to have their α-amino groups and side chain functionalities (if present) differentially protected such that the α-amino protecting group may be selectively removed during the synthesis. The coupling of an amino acid is performed by activation of its carboxyl group as an active ester and reaction thereof with the unblocked α-amino group of the N-terminal amino acid appended to the resin. The sequence of α-amino group deprotection and coupling is repeated until the entire peptide sequence is assembled. The peptide is then released from the resin with concomitant deprotection of the side chain functionalities, usually in the presence of scavengers to limit side reactions. The resulting peptide is finally purified by reverse phase HPLC.

The synthesis of the peptidyl-resins required as precursors to the final EBP peptides utilize commercially available cross-linked polystyrene polymer resins. Preferred for use in this invention is 4-(2',4'-dimethoxyphenyl-Fmoc-aminomethyl)-phenoxyacetyl-p-methyl benzhydrylamine resin (Rink amide MBHA resin), Novabiochem, San Diego, Calif. Coupling of amino acids can be accomplished using HOBT or HOAT active esters produced from HBTU/HOBT in the presence of a tertiary amine such as DIEA, or from DIC/HOAT, respectively.

Preferred Fmoc amino acids for use in synthesizing the EBPs of the present invention are the derivatives shown below.

Orthogonally Protected Amino Acids Used in Solid Phase Synthesis

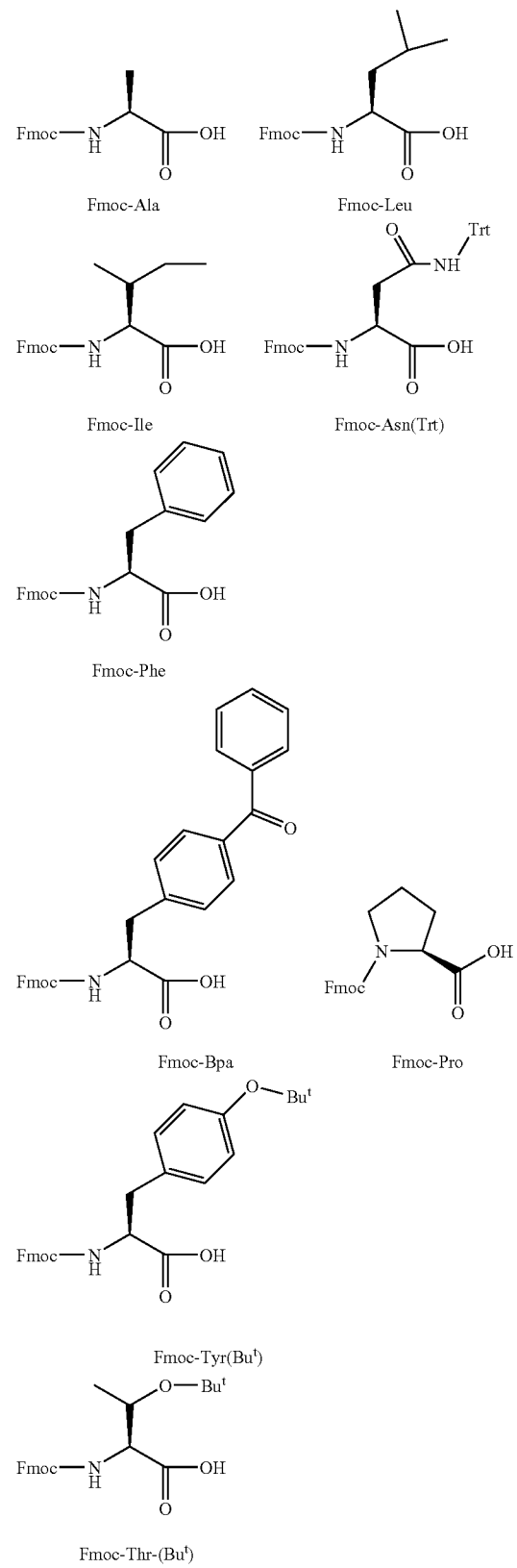

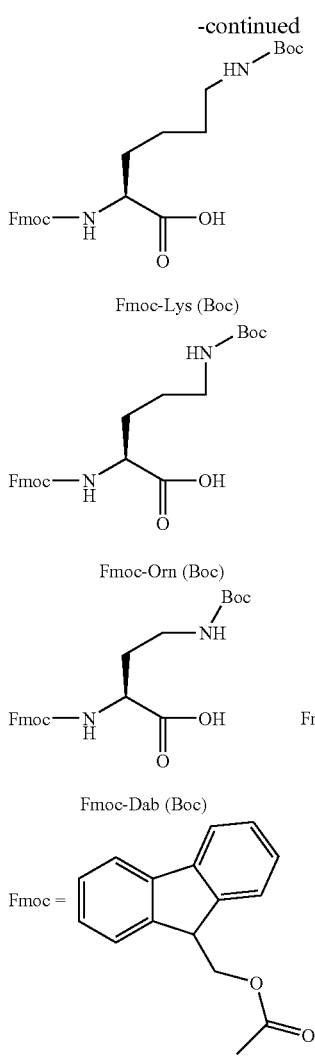

Fmoc-Lys (Boc)

Fmoc-Orn (Boc)

Fmoc-Dab (Boc)    Fmoc-Dap (Boc)

Fmoc =

The peptidyl-resin precursors for their respective peptides may be cleaved and deprotected using any of the standard procedures described in the literature (see, for example, King et al., (1990) *Int. J. Peptide Protein Res.* 36:255-266). A preferred method for use in this invention is the use of TFA in the presence of water and TIS as scavengers. Typically, the peptidyl-resin is stirred in TFA/water/TIS (94:3:3, v:v:v; 1 mL/100 mg of peptidyl resin) for 1.5-2 hrs at room temperature. The spent resin is then filtered off and TFA solution is concentrated or dried under reduced pressure. The resulting crude peptide is either washed with $Et_2O$ or redissolved directly into DMSO or 50% aqueous acetic acid for purification by preparative HPLC.

Peptides with the desired purity can be obtained by purification using preparative HPLC on, for example, either a Waters Model 4000 or a Shimadzu Model LC-8A liquid chromatograph. The solution of crude peptide is injected into a YMC S5 ODS (20×100 mm) column and eluted with a linear gradient of MeCN in water, both buffered with 0.1% TFA, using a flow rate of 14-20 mL/min with effluent monitoring by UV absorbance at 220 nm. The structures of the purified peptides are typically confirmed by electrospray MS analysis.

Attachment of a fluorescent label to the EBP peptides described herein may be accomplished by reacting either the α-amino group of the N-terminal amino acid residue of the EBP peptide or the ω-amino group of the side chain of a α,ω-diamino acid appended to the C-terminus of a EBP peptide with the N-hydroxysuccinimidyl ester derivatives of the desired fluorophore. Preferred for use in this invention is the Alexa Fluor 488 fluorophore ("Alexa488") (Molecular Probes, Eugene, Oreg.).

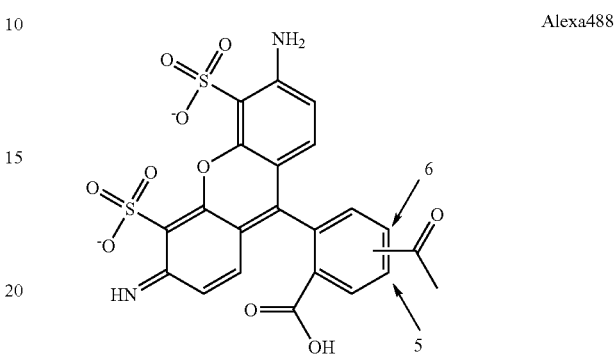

Alexa488

The following abbreviations are employed in the Examples and elsewhere herein:

TMS=trimethylsilyl; FMOC=fluorenylmethoxycarbonyl; Boc or BOC=tert-butoxycarbonyl; Bpa=p-benzoyl phenylalanine; HOAc or AcOH=acetic acid; MeCN=acetonitrile; DMF=N,N-dimethylformamide; TFA=trifluoroacetic acid; TIS=Triisopropylsilane; $Et_2O$=diethyl ether; NMP=N-methylpyrrolidone; DCM=dichloromethane; HOBT=1-hydroxybenzotriazole; HOAT=1-hydroxy-7-azabenzotriazole; HBTU=2-(1H-Benzotriazole-1-yl)-1,1,3,3-tetramethyluronium hexafluorophosphate; DIC=N,N'-diisopropylcarbodiimide; DIEA=N,N-diisopropylethylamine; min=minute(s); h or hr=hour(s); L=liter; mL=milliliter; μL=microliter; g=gram(s); mg=milligram(s); mol=mole(s); mmol=millimole(s); meq=milliequivalent; rt=room temperature; sat or sat'd=saturated; aq.=aqueous; HPLC=high performance liquid chromatography; LC/MS=high performance liquid chromatography/mass spectrometry; MS or Mass Spec=mass spectrometry.

In accordance with the present invention, isolated and/or synthetic EBPs can also be used to identify BACE exosites, and are a useful tool for characterizing the structure of BACE exosites. For example, a BACE exosite may be characterized by crosslinking an EBP tagged with a photoaffinity group or photoaffinity label to the BACE exosite. The terms "photoaffinity group" and "photoaffinity label" refer to a substituent on the inhibitor which can be activated by photolysis at an appropriate wavelength to undergo a crosslinking photochemical reaction with BACE. An example of a "photoaffinity group" is a benzophenone substituent.

In another embodiment of the present invention, the EBPs can be used as a BACE probe.

The following definitions apply to the terms used throughout this specification, unless otherwise defined in specific instances:

The term "BACE" as used herein refers to all forms of BACE, including BACE variants and proteins including the catalytic domain of BACE, or a fragment of BACE containing a BACE exosite. A representative, but non-limiting, example of BACE is a protein encoded by all or a fragment of the nucleic acid of GenBank Accession No. NM012104.

"Modulator of BACE" or "BACE modulator" as used herein refers to a compound that alters the activity of BACE, such as, for example, agonists that increase the activity of BACE or antagonists that inhibit the activity of BACE.

The term "compound" as used herein includes but is not limited to small molecules, peptides, nucleic acid molecules and antibodies.

As used herein, "candidate modulator of BACE" is intended to mean any compound that can be screened for activity to inhibit BACE using the assay of the invention described herein. It is understood that a "candidate modulator of BACE", which is active in the assay of the invention for inhibiting BACE activity, can subsequently be used as a "BACE modulator" or "BACE inhibitor". It is also understood that a "candidate modulator of BACE", which is active in the assay of the invention for inhibiting BACE activity, can subsequently be used in pharmaceutical compositions for the treatment of degenerative neurological disorders involving beta-amyloid production, preferably for the treatment of Alzheimer's disease.

As used herein, "candidate inhibitor of beta-amyloid production" is intended to mean any compound that can be screened for activity to inhibit the production of beta-amyloid peptide, or the proteolytic activity leading to the production of beta-amyloid peptide, using the assay of the invention described herein. It is understood that a "candidate inhibitor of beta-amyloid production", which is active in the assay of the invention for inhibiting the production of beta-amyloid peptide, can subsequently be used as a "beta-amyloid peptide inhibitor." It is also understood that a "candidate inhibitor of beta-amyloid production", which is active in the assay of the invention for inhibiting the production of beta-amyloid peptide, can subsequently be used in pharmaceutical compositions for the treatment of degenerative neurological disorders involving beta-amyloid production, preferably for the treatment of Alzheimer's disease.

The "inhibitory concentration" of a BACE modulator or inhibitor is intended to mean the concentration at which a compound screened in an assay of the invention inhibits a measurable percentage of BACE activity. Examples of "inhibitory concentration" values range from $IC_{50}$ to $IC_{90}$, and are preferably, $IC_{50}$, $IC_{60}$, $IC_{70}$, $IC_{80}$, or $IC_{90}$, which represent 50%, 60%, 70%, 80% and 90% reduction in BACE activity, respectively. More preferably, the "inhibitory concentration" is measured as the $IC_{50}$ value. It is understood that another designation for $IC_{50}$ is the half-maximal inhibitory concentration.

Likewise, as used herein, "inhibitory concentration" of a beta-amyloid production inhibitor is intended to mean the concentration at which a compound screened in an assay of the invention inhibits a measurable percentage of beta-amyloid peptide production. Examples of "inhibitory concentration" values range from $IC_{50}$ to $IC_{90}$, and are preferably, $IC_{50}$, $IC_{60}$, $IC_{70}$, $IC_{80}$, or $IC_{90}$, which represent 50%, 60%, 70%, 80% and 90% reduction in beta-amyloid peptide production, respectively. More preferably, the "inhibitory concentration" is measured as the $IC_{50}$ value. It is understood that another designation for $IC_{50}$ is the half-maximal inhibitory concentration.

The EBPs of the present invention are particularly useful for identifying inhibitors of Aβ production. The EBPs can be used in competitive binding assays to identify inhibitors of proteolytic activity leading to Aβ production for the treatment of neurological disorders, such as Alzheimer's disease, Down's syndrome and other disorders involving Aβ, APP, and/or Aβ/APP associated macromolecules. Such competitive binding assays can identify compounds that interfere with the binding of EBPs to isolated BACE, complexes of BACE and other macromolecules, relevant tissues, cell lines, and membranes derived from relevant tissues and cell lines.

In one embodiment, the present invention provides a method for identifying modulators of BACE comprising the steps of:

(a) contacting a candidate modulator of BACE and an exosite binding peptide (EBP) in the presence of a BACE including at least one BACE exosite; and (b) determining whether there is a decrease in binding of the exosite binding peptide to BACE in the presence of the candidate BACE modulator compared to binding of the exosite binding peptide to BACE in the absence of the candidate modulator.

The binding to and displacement from BACE of exosite binding peptides (EBPs) can be determined by methods well known to those skilled in the art. The form of BACE used for such experiments can be recombinant or natural full length BACE within the environment of a cellular membrane, or solubilized from a membrane by appropriate treatment with a detergent. Alternatively, the purified, recombinant catalytic domain of BACE can be used in the binding measurements. BACE molecules such as for example, allelic variants, fragments, or fusion proteins including at least one BACE exosite of interest are within the scope of the invention for use in the screening assays herein. In a preferred embodiment of the present invention BACE is recombinant human BACE catalytic domain as described in Mallender et al., (2001) *Mol. Pharmacol.* 59:619-626, and as described herein in Example 3.

Binding of the EBPs to BACE can be measured, for example, by methods such as isothermal titration calorimetry, nuclear magnetic resonance spectroscopy, BIAcore technology and the like. In a preferred embodiment, the EBPs can be modified by the incorporation of a chromophoric, fluorophoric or radioactive species to provide a convenient label with which to follow the interactions of the peptides with the macromolecular enzyme. As an example, a fluorescent molecule can be covalently attached to the amino terminus, to the carboxyl terminus, or to specific amino acid side chains (e.g., lysines and cysteines) of the peptide by application of standard peptide chemistry that is well known to those skilled in the art. For example, the EBP can be labeled with Alexa488 (Molecular Probes, Eugene, Oreg.). Once labeled and purified, the now fluorescent EBP can be conveniently used to measure formation of a binary complex with the BACE molecule.

In one aspect of the present invention, the fluorescent EBP can be mixed with BACE under conditions that optimally promote binding, for a sufficient time to establish an equilibrium between the bound and free forms of the enzyme and peptide. The free peptide can then be rapidly separated from the enzyme-bound population by any of several methods that effect separation of molecules based on molecular mass, such as gel filtration chromatography, dialysis and membrane filtration. The amount of fluorescent EBP associated with the enzyme can then be quantified by fluorescence spectroscopy. By measuring the concentration of EBP bound to the enzyme as a function of enzyme and EBP concentration, the equilibrium dissociation constant, $K_d$, for the enzyme-EBP binary complex can be determined by standard methods well known to those trained in the art (see, for example, Copeland, R. A., *Enzymes: A Practical Introduction to Structure, Mechanism and Data Analysis*, ($2^{nd}$ ed.), Wiley-VCH, New York, N.Y. (2000)). Having determined the $K_d$, one can mix a specific concentration of BACE and EBP to establish a particular level of EBP occupancy on BACE. Addition of compounds that compete with EBPs for binding to BACE would cause a shift in the fractional occupancy of the fluorescent EBP on BACE. By measuring the shift in fractional occupancy as a function of the concentration of competing compound, one can define the $K_d$ of the competing compound by methods well known to those skilled in the art (see, for example, Copeland, R. A., *Enzymes: A Practical Introduction to Structure, Mechanism and Data Analysis*, ($2^{nd}$ ed.), Wiley-VCH, New York, N.Y. (2000)).

Often, the fluorescence properties of a molecule will change upon complex formation with a protein. Hence, changes in a fluorescence emission wavelength maximum or fluorescence intensity may accompany binding of the labeled EBP to BACE. In such cases, the change in fluorescence property can be used as a direct measure of binding, without the need to physically separate the bound and free populations of labeled EBP.

In a preferred embodiment, the polarization (or anisotropy) of fluorescence is measured with a suitable instrument. The degree of fluorescence polarization depends on the rotational freedom of the fluorescent molecule. When free in solution the fluorescence polarization of the labeled EBP would have a characteristic low value. Upon complexation with BACE, the rotational freedom is diminished and the degree of fluorescence polarization increases markedly. These changes in characteristic fluorescence polarization can therefore be used to measure the fractional occupancy of EBPs on BACE and, as described above, can also be used to measure the binding affinity of competing molecules. In a manner similar to that described above, a fixed concentration mixture of BACE and labeled EBP is mixed with varying concentrations of a competing compound. Displacement of the EBP caused by competition with the compound for the binding site on BACE is quantified by the changes in fluorescence polarization value.

Alternatively, a fluorescent or chromophoric molecule can be covalently associated with the BACE enzyme through standard protein chemistry methods that are well known to those skilled in the art. The spectroscopic features of the molecule are chosen to overlap those of a fluorescent group attached to the EBP as described above, such that the absorbance maximum of the species attached to the enzyme overlaps the fluorescence maximum of the species attached to the EBP. When the enzyme and EBP are separate, the maximal fluoresence of the species attached to the EBP is realized. However, when the binding of the EBP to BACE brings the spectroscopic species attached to BACE and the EBP into proximity, the overlap of spectral properties will cause a diminution of fluorescence intensity for the group attached to the EBP in what is commonly referred to as Fluorescence Resonance Energy Transfer (FRET). The diminution of fluorescence intensity that accompanies binding between BACE and the EBP can be directly quantified as a measure of binding interactions. The addition of a competing molecule to a mixture of the BACE/EBP FRET pair would cause a relief of the fluorescence intensity quenching which could thus be used to measure competitive binding of compounds to the EBP binding site on BACE.

In yet another embodiment, the EBP is labeled by incorporation of a radioactive species, such as $^3H$, $^{14}C$, $^{35}S$, $^{33}P$, $^{125}I$, etc., by standard methods of peptide chemistry. In a manner similar to that described above, the binding of the radiolabeled EBP to BACE can be followed by mixing the peptide and protein together under optimal conditions and then rapidly separating the free peptide population from the enzyme-bound population.

In a further embodiment of the present invention an affinity sequence can be appended to the amino acid sequence of the BACE enzyme using standard methods of recombinant DNA technology. Examples of such affinity sequences include, but are not limited to multiple histidine residues for complexation with transition metals, epitopic sequences that are recognized by specific antibodies, and biotin which is recognized by the protein streptavidin. Technology well known to those skilled in the art commonly referred to as a Scintillation Proximity Assay (SPA) can be used to measure binding of the labeled EBP to BACE and the displacement of this binding by competing molecules.

Polymeric beads that are saturated with scintillation fluid and are chemically attached to the recognition partner of the affinity sequence, i.e., chemically attached to a transition metal, a specific antibody, or to streptavidin or other recognition partners, can be mixed with the BACE protein containing the affinity sequence to form a stable complex between the BACE protein and the polymeric bead. When radiolabeled EBP is added to this mixture, the binding of the EBP to BACE brings the radiolabel on the peptide into close proximity with the scintillation fluid incorporated into the polymeric bead. The resulting light emission from the scintillation fluid can then be quantified as a measure of binding interaction between BACE and the peptide. In a manner similar to that outlined above, the signal measured in this way can be used to quantify binding of the labeled EBP to BACE and the displacement of this binding by competing molecules.

Any of the above methods can be adapted for use in high throughput screening of compound libraries to discover molecules that compete with the EBP for binding to the exosite on BACE. Standard methods can be used to adapt the methods described above for measurements in micro-well plates of varying formats including, but not limited to, 96, 384 and 1536 wells per plate. In a common high throughput screening application, the BACE enzyme and EBP are mixed at fixed concentrations in each well of the micro-well plate. To individual wells of each plate is added one compound of a compound library at a fixed concentration. After mixing the signal associated with BACE/EBP complex formation is measured by use of an appropriate microplate reading instrument. Library compounds that alter the signal associated with BACE/EBP complex formation can thus be identified as potential competitors for the EBP binding site on BACE. These library compounds can then be characterized further to determine their individual binding affinity for BACE by the more complete methods described above.

The present invention provides a method for identifying inhibitors as therapeutics for disorders involved in APP processing and beta-amyloid production comprising:

(a) contacting BACE with a candidate BACE exosite binding compound; and (b) determining the amount of inhibition of APP processing and beta-amyloid production.

The present invention provides a cell based assay for identifying BACE exosite binding compounds that inhibit beta-amyloid production comprising:

(a) contacting a candidate BACE exosite binding compound with a cell that expresses a beta amyloid precursor protein and BACE wherein the cell is capable of secreting beta-amyloid protein in the absence of the candidate exosite binding compound; and (b) determining whether the candidate exosite binding compound reduces the amount of beta amyloid protein secreted by the cell.

In another embodiment of the invention, the method for identifying BACE exosite binding compounds that inhibit beta-amyloid production is performed using cell membranes or in a cell-free setting using cell-free enzyme and cell-free substrate according to methods known to those skilled in the art.

The present invention provides EBPs that bind to a BACE exosite and inhibit BACE activity. Inhibition of BACE activity by the EBPs of the present invention can be demonstrated using beta-amyloid precursor protein (also referred to herein as "β-APP" or "APP"), the precursor for Aβ, which through the activity of secretase enzymes is processed into Aβ. Secretase enyzmes known in the art have been designated β secretase, which generates the N-terminus of Aβ, α secretase cleaving around the 16/17 peptide bond in Aβ, and γ secretase which generates C-terminal Aβ fragments ending at position 38, 39, 40, 41, 42, and 43, or C-terminal extended precursors which are subsequently truncated to the above peptides.

In accordance with the present invention, full length human APP, known mutations thereof (e.g., the Swedish mutant), fragments of human wild type or mutant APP, peptides derived from human wild type or mutant APP as well as APP or APP fragments fusion proteins, such as, MBP-APP (which includes APP residues 547-595) can be used as a substrate to confirm inhibition of BACE activity by an EBP. The peptide bond hydrolysis activity of BACE can be determined by contacting an appropriate substrate with the enzyme under optimized reaction conditions and then measuring the loss of substrate or production of hydrolysis products as a function of reaction time by some suitable analytical detection method. For example, the recombinant catalytic domain of human BACE can be incubated with the peptide MCA-EVNLDAEFK(-dnp)-COOH (SEQ ID NO:107) in which MCA is a 7-methoxycoumarin-4-acetyl group and dnp is a dinitrophenyl group appended to the epsilon amino group of the lysine side chain. This peptide sequence reflects the amino acid sequence surrounding the beta cleavage site of Swedish mutant APP. The MCA group is highly fluorescent but its fluorescence is quenched by proximity to the dnp group. Thus, the peptide displays low fluorescence signal when intact, but the fluorescence signal is greatly augmented upon BACE-mediated hydrolysis of the peptide.

After a fixed time of incubation, the increase in fluorescence signal can be used as a measure of BACE activity, as described more fully in Mallender et al., (2001) *Mol. Pharmacol.* 59:619-626 and in Marcinkeviciene et al., (2001) *J. Biol. Chem.* 276, 23790-23794. The ability of an EBP to inhibit the BACE-mediated hydrolysis of this substrate would be reflected in a diminished fluorescence signal after substrate incubation with BACE in the presence of the EBP.

Such assays can be performed in a cell free setting, using cell-free enzyme and cell-free substrate, or can be performed in a cell-based assay, or using cell membranes according to methods known to those skilled in the art.

The present invention further provides a method of treating a neurological disorder comprising administering to a patient in need of such treatment a therapeutically effective amount of a compound that inhibits beta-amyloid production, or a pharmaceutically acceptable salt or prodrug form thereof, wherein the compound binds to a BACE exosite and effects a decrease in production of beta-amyloid.

The compounds determined from the present invention can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is *Remington's Pharmaceutical Sciences* (17$^{th}$ ed.), Mack Publishing Co., Easton, Pa., (1985).

The compounds determined from the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to beta-amyloid production or accumulation, such as Alzheimer's disease and Down's Syndrome.

The compounds of this invention can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds determined from the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds determined from the present invention may be administered in a single daily dose, or the total daily dosage may be administered in divided doses of two, three, or four times daily.

The compounds identified using the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present invention, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds determined from the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamide-phenol, or polyethyleneoxide-polylysine substituted with palmitoyl residues.

Furthermore, the compounds determined from the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like.

Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in *Remington's Pharmaceutical Sciences* (1985).

EXAMPLES

The following examples as set forth herein are meant to illustrate and exemplify the various aspects of carrying out the present invention and are not intended to limit the invention in any way.

The synthetic peptides described herein were prepared as N-terminal acetyl derivatives and as C-terminal carboxy amides, with the exception of those peptides identified as SEQ ID NOs:19 and 48, which were prepared as N-terminal acetyl derivatives but did not contain a C-terminal carboxy amide group.

Example 1

BACE Exosite Binding Peptides from Solid Phase Panning at pH 7.0.

Two highly selected and homologous 12 mer phage peptides bound BACE specifically and reproducibly in phage-ELISA tests. Bristol-Myers Squibb fUSE5-based C4C, C6C, 5- and 15 mer libraries, and M13-based C7C libraries, and 7- and 12 mer libraries obtained from New England Biolabs, Beverly, Mass. were panned for three cycles against BACE (produced as described herein in Example 3). BACE was immobilized by coating at 0.5 µg/well in 4 wells of Dynex Immulon 4HBX plates overnight at 4° C. in 0.1M NaHCO$_3$ buffer, pH 9.0. Panning was by standard procedures at room temperature that involved blocking wells with 2% BSA in PBS and elution with 0.1M HCL, pH 2.2. The vector NTI alignment tool and visual inspection of sequences were employed to analyze the selected peptides.

After sequencing approximately 20-50 clones from each library after three cycles of selection, we prepared essentially all possible candidate clones (39 clones in total) for phage-ELISA to obtain direct evidence for affinity to BACE. Eleven clones gave binding signals and one of those clones, a 12 mer clone (NLTTYPYFIPLP (SEQ ID NO:19)), was reproducibly shown to specifically bind to BACE. We therefore sequenced additional 12 mer clones to try to find additional candidate clones. Eleven candidate clones were tested by phage ELISA and one clone (ALYPYFLPISAK (SEQ ID NO:20)) exhibited specific binding to BACE. This AL<u>YPYFLPIS</u>AK (SEQ ID NO:20) peptide is homologous to NLTT<u>YPYFIPL</u>P (SEQ ID NO:19) and consistent with the specific binding of both those peptides to BACE. The ALYPYFLPISAK (SEQ ID NO:20) peptide and NLTTYPYFIPLP (SEQ ID NO:19) peptides were the two most efficiently recovered clones with 13 and 9 copies, respectively.

Example 2

BACE Binding Peptides from Solid- and Solution Phase Panning at pH 5.0.

Solid phase panning experiments at pH 7.0 yielded exosite BACE binding peptides BMS-561871 and BMS-561877 which share a conserved core region. Solution and solid phase panning at pH 5.0 yielded 21 peptides with essentially the same conserved core region that is present in BMS-561871 and BMS-561877. Overall, solution phase panning appeared to facilitate the isolation of these peptides. This is consistent with the idea that the peptide binding site on BACE may be less accessible when BACE is immobilized, as in solid phase panning. The presence of the active site inhibitor OM99-2 in solid phase panning did not noticeably improve the ability to recover these peptides. In the absence of OM99-2, any selection for peptides that occupy the active site of BACE may therefore be less efficient or absent. The results are consistent with the idea that the new set of peptides binds BACE outside the active site.

Phage ELISA indicated that all 21 peptides from the solid phase panning bind BACE specifically at pH 5.0 and pH 7.0. Binding specificity for peptides from solution phase was only tested at pH 5.0 and where signals were obtained (subject to phage concentrations which were not standardized), peptides bound specifically. Consensus peptides are provided at the end of Table 1. The presence of a histidine residue immediately flanking the YPYF (SEQ ID NO:1) motif, i.e. HYPYF (SEQ ID NO:8), appears to contribute to more efficient binding at pH 5.0. BMS-561871 and BMS-561877 were isolated at pH 7.0 and lack histidine at this position.

Peptides with Other Sequence Motifs

Two tight-binding peptides contained a conserved region that is significantly different from, but clearly related to the core region in BMS-561871 and BMS-561877. Solid- and solution phase panning yielded 6 and 4 groups of peptides, respectively, that contained motifs other than the YPYF motif in the peptides listed in Table 1. Two peptides from solution panning, ETWPRFIPYHALTQQTLKHQQHT (SEQ ID NO:22) and TAEYESRTARTAPPAPTQHW-PFFIRST (SEQ ID NO:23), exhibited strong and specific binding that was similar to phage carrying BMS-561871. The ET<u>WPRFI</u>PYHALTQQTLKHQQHT (SEQ ID NO:22) and TAEYESRTARTAPPAPTQH<u>WPFFI</u>RST (SEQ ID NO:23) BMS-561871 peptides include a WPXFI (SEQ ID NO:21) motif. The result is consistent with the fact that the two peptides ETWPRFIPYHALTQQTLKHQQHT (SEQ ID NO:22) and TAEYESRTARTAPPAPTQHWPFFIRST (SEQ ID NO:23) from solution panning share a region with homology that is different from, but clearly similar to, the core region of the peptides ALYPYFLPISAK (SEQ ID NO:20) and NLTTYPYFIPLP (SEQ ID NO:19). Thus, peptides containing the YPYF (SEQ ID NO:1) motif or closely related sequences are able to efficiently bind BACE at the BACE exosite.

Panning a.) Solid Phase:

The M13-based C7C-, 12-, and 15 mer libraries were panned in the presence or absence of 1 μM OM99-2 against BACE produced as BACE-IgG$_1$ from CHO cells and treated to remove the Ig-domain, as described in Example 3. Three panning cycles were carried out: BACE was immobilized at 0.5 μg/well in 4 wells of Dynex Immulon plates overnight in 0.1M NaHCO$_3$ buffer, pH 9.0. This was followed by blocking the wells with PBS+2% BSA for 1 hour. For panning at pH 5.2, blocking buffer was discarded and library phage was then added for two hours in 50 mM NaOAc, pH 5.2+2% BSA, followed by washes with 50 mM NaOAc, pH 5.2, +0.2% Tween 20 and subsequent elution with 0.1M HCl, pH 2.2 for amplification or DNA sequencing after round three. For panning at pH 7.0, all buffers were based on PBS instead of NaOAc.

b.) Solution Phase:

The following mixtures of our M13-based libraries were panned against BACE-prepared from CHO cells (vide supra): a.) C7C+C8C libraries, b.) 12-+15 mer libraries, and c.) 23-+27-+33 mer libraries. Library mixtures and BACE were pre-blocked in 50 mM NaOAc, pH 5.2, +2% BSA and then mixed for two hours. The mixtures were then added to Pansorbin Protein A cells (Calbiochem) in 50 mM NaOAc, pH 5.2, after blocking the cells in NaOAc, pH 5.2, plus 2% BSA and 1% milk. This step was followed by washing the Pansorbin cell-phage complexes several times with 50 mM NaOAc, pH 5.2, plus 0.2% Tween 20. Phage were eluted with 6M urea, pH 3.0, and used for amplification and further panning cycles or DNA sequencing after round three.

Phage ELISA

Standard procedures were used: BACE (without IgG, domain) was coated in 0.1M NaHCO$_3$, pH 9.0 overnight at 4° C. From this point onwards, all incubation and wash buffers were based on 50 mM NaOAc, pH 5.2, for determining binding at pH 5.2. To determine binding at pH 7.0, NaOAc was replaced by PBS.

TABLE 1

Peptides Having a YPYF Motif Specifically Bind to a BACE Exosite

SOLID PHASE PANNING AT pH 7.0:

NLTT*YPYF*IPLP (BMS-561871) (SEQ ID NO:19)

AL*YPYF*LPISAK (BMS-561877) (SEQ ID NO:20)

SOLID PHASE PANNING AT pH 5.0:

QNH*YPYF*IAVPI (SEQ ID NO:24)

EGNKH*YPYF*IKV (SEQ ID NO:25)

THSH*YPYF*IELE (SEQ ID NO:26)

QQ*YPYF*IPVIRP (SEQ ID NO:27)

SOLUTION PANNING AT pH 5.0:

H*YPYF*LPLHTPK (SEQ ID NO:28)

AMLDGAPTNRNSQH*YPYF*LPIATV (SEQ ID NO:29)

TABLE 1-continued

Peptides Having a YPYF Motif Specifically Bind to a BACE Exosite

| | |
|---|---|
| LPVYDTTAPTH*YPYF*LPLPRISP | (SEQ ID NO:30) |
| EGNKH*YPYF*IKV | (SEQ ID NO:25) |
| SQLQH*YPYF*RPL | (SEQ ID NO:31) |
| YIPH*YPYF*IRLN | (SEQ ID NO:32) |
| KMHSMINQLGTRH*YPYF*REINDY | (SEQ ID NO:33) |
| GSTKS*YPYF*IHT | (SEQ ID NO:34) |
| DIWNGAKAPKNSM*YPYF*IPSSLK | (SEQ ID NO:35) |
| ISVINQPAQNMHPRQMTA*YPYF*RPISR | (SEQ ID NO:36) |
| DV*YPYF*VSSNEGHSIRHKGNNSL | (SEQ ID NO:37) |
| *YPYF*IDSHPPKELMPHSWVQSKYPASPQTHTTY | (SEQ ID NO:38) |
| G*YPYF*LNLKNSH | (SEQ ID NO:39) |
| NS*YPYF*IHLSNP | (SEQ ID NO:40) |
| HD*YPYF*MMLTGH | (SEQ ID NO:41) |
| QIET*YPYF*LPIL | (SEQ ID NO:42) |
| Y*YPYF*ISTAREV | (SEQ ID NO:43) |

Consensus:

| | | |
|---|---|---|
| H*YPYF*IPL | | (SEQ ID NO:18) |
| Y | L | I |
| T | V | V |
| S | M | |

TABLE 2

Peptides with Other Sequence Motifs
SOLUTION PHASE PANNING AT pH 5.0:

| | |
|---|---|
| ETWPRFIPYHALTQQTLKHQQHT | (SEQ ID NO:22) |
| TAEYESRTARTAPPAPTQHWPFFIRST | (SEQ ID NO:23) |

Example 3

Isothermal Titration Calorimetry (ITC) of BACE and Exosite Peptides

Isothermal titration calorimetry was performed to determine quantitatively the binding affinities of BMS-561877 and BMS-561871 for β-secretase. Recombinant human BACE was expressed as a fusion protein with human IgG$_1$, in Chinese hamster ovary (CHO) cells (Vassar et al., (1999) *Science* 286:735-741 and Haniu et al., (2000) *J. Biol. Chem.* 275:21099-21106).

This construct, referred to as BACE-T-IgG, also contained a protease cleavage site between BACE and IgG$_1$, sensitive to human α-thrombin. The cDNA for the catalytic domain of human BACE (residues 1-460) was PCR-amplified and subcloned into the mammalian expression vector pTV1.6, upstream of a thrombin cleavage site linked to cDNA encoding human IgG$_1$ heavy chain. The vector construct, pTV1.6-BACE-T-IgG, was used to produce stably transfected DHFR-deficient CHO DG44 cells, which were then scaled up using methotrexate for selection.

The clarified growth media harvested from CHO DG44 cells which contained the fusion protein was loaded onto a rProtein A SEPHAROSE™ column (5×20 cm, Amersham Pharmacia Biotech) using a peristaltic pump at 4° C., at 4 mL/min. The column was washed with Dulbecco's PBS, pH 7.1, 4 mL/min, until baseline absorbance at 280 nm was observed. BACE-T-IgG was eluted from the resin with 0.10 M citrate, pH 3.0, into tubes containing 0.5 volumes of 4 M Tris, pH 8. Fractions containing the fusion protein were dialyzed extensively using 12,000-14,000 kDa MWCO membrane (UltraPURE, GIBCO BRL) against PBS, pH 7.1, at 4° C. The protein was sterile filtered (0.22 μm) and stored at 4° C.

To generate BACE for binding experiments, the fusion protein BACE-T-IgG was treated with human α-thrombin (Enzyme Research Labs, South Bend, Ind.) at a ratio of 1:500 (mass:mass) in Dulbecco's PBS, pH 7.1, at 37° C. for 2 hr. Human α-thrombin was removed by passing the sample over Benzamidine SEPHAROSE™ 6B column (Amersham Pharmacia Biotech). The cleaved IgG$_1$ was captured by passing the solution over a rProtein A SEPHAROSE™ (Amersham Pharmacia Biotech) column, whereas the BACE passed through this column. The protein sample was further purified by concentrating to 10-15 mg/mL using a centrifugation concentration unit (Millipore Ultrafree 10 kDa MWCO, 15 mL unit) and loading onto a SUPERDEX™ 200 PC 3.2/30 gel-filtration column (Amersham Pharmacia Biotech). The column was run at 3 mL/min with Dulbecco's PBS, pH 7.1, at room temperature. Fractions containing BACE were combined, sterile filtered (0.22 μm) and stored at 4° C. The protein was characterized by SDS-PAGE and other biophysical techniques, including UV-vis spectrometry, dynamic and static light scattering, to demonstrate that it was glycosylated and monomeric. Amino-terminal sequencing indicated a mixture of two start sequences, LPRET- and ETDEE-, the latter of which is the expected sequence for the mature sequence of the protease (Haniu et al., (2000) *J. Biol. Chem.* 275:21099-21106).

BACE was prepared for isothermal titrating calorimetry by extensive dialysis against fresh buffer at 4° C. using 12,000-14,000 kDa MWCO dialysis membrane (Ultra-PURE, GIBCO BRL). The buffer was either Dulbecco's PBS (2 mM $KH_2PO_4$, 8 mM $Na_2HPO_4$, 137 mM NaCl, 3 mM KCl), pH 7.1, or 25 mM NaOAc, containing 137 mM NaCl and 3 mM KCl, pH 5.3. Following 2 buffer changes, the protein was removed from the membrane and centrifuged (5 min×4000 g, 4° C.) to remove particulates. The protein was stored at 4° C. until needed for the calorimetry experiments. The protein concentration was determined by 10-fold dilution into the same buffer, and measuring the UV absorbance at 280 nm in a 1.00 cm pathlength cell (calculated value=1.22 AU=1.00 mg/mL protein, based on mean glycosylated molecular weight=53.5 kDa, and given amino acid composition). Final concentrations used in isothermal titrating calorimetry were typically 5.0 μM, containing a final concentration of 0.5% v/v DMSO.

Peptides were dissolved in the buffer dialysate from protein dialysis, and equal volumes of DMSO were added to each (0.5% v/v DMSO). The pH values of the solutions were adjusted as necessary to equal that of the buffer dialysate and protein sample within 0.01 pH units. The concentrations of peptides NLTTYPYFIPLP (SEQ ID NO:19) and ALYPYPLPISAK (SEQ ID NO:20) were determined by diluting 10-fold in the same buffer and measuring the UV absorbance at 276 nm, using the value of $\epsilon=2780$ $M^{-1}cm^{-1}$ (or $2\times1390$ $M^{-1}cm^{-1}$ for 2 Tyr residues per peptide).

The active site inhibitor peptide OM99-2 was obtained from Bachem (King of Prussia, Pa.) as a dry white powder. The compound was weighed into a clean polypropylene tube (1.7 mL) and DMSO was added to prepare a stock solution of 10.0 mM. This stock sample was diluted in buffer (protein dialysate) to ~50 μM containing a final concentration of 0.5% v/v DMSO for titration experiments.

Isothermal titrating calorimetry experiments were performed with a VP-ITC instrument from MicroCal, Inc. (Northampton, Mass.). The instrument was controlled with a personal computer, and thermally regulated at the desired experimental temperature (25° C. or 37° C.). Samples of BACE and peptides were degassed for 2×5 min at 15° C. using a temperature-regulated degassing unit (MicroCal) before loading into the sample chamber or syringe, respectively. Deionized, degassed water was loaded into the instrument reference chamber and used for all experiments. For each titration experiment, a fresh sample of BACE (typically 5.0 μM, 2.0 mL) was loaded into the instrument sample chamber (volume=1.438 mL), using a glass syringe, following the manufacturer's directions. Similarly, fresh peptide samples (typically ~150 μM for peptides NLTTYPYFIPLP (SEQ ID NO:19) and ALYPYPLPISAK (SEQ ID NO:20) and ~50 μM for OM99-2, 0.3 mL total volume) were loaded into the instrument injecting syringe unit before each experiment. For experiments to demonstrate that the active site directed inhibitor peptide OM99-2 and the peptide NLTTYPYFIPLP (SEQ ID NO:19) did not compete for the same site, a 10-fold excess of desired peptide was first added to a fresh sample of BACE and incubated at room temperature for 5 min before degassing and loading into the instrument. Titrations were then performed with the other peptide in the syringe.

Instrument Parameters

The temperature was maintained at 25° C. or 37° C. during the titration experiments. A power setting of 6.0 μCal/sec was used, and a syringe stirring rate of 300 rpm was used. The initial injection was kept at 1.5-2.0 μL and the data from this injection was not included in the analysis as a standard practice. To completely define the binding isotherm, typically a 2.5-fold to 3.5-fold excess of peptide was added during the course of the titration experiment, using about 15 injections per molar equivalent, or 3.0 μL (NLTTYPYFIPLP, SEQ ID NO:19) or 6.0 μL (OM99-2) per injection. The data collection time per injection was fixed at 360 sec, with a signal averaging time of 2 sec. The data was analyzed using the manufacturer's software fitting to a single site binding model (i.e. Origin 5.0 for ITC). Before molar heat calculations were done, background corrections were made on all peaks by subtracting the mean of the final 10-15 injections from all injections.

The calculated molar heat values were fitted to a single binding site model using the manufacturer's software to determine the binding stoichiometry (n), the association constant ($K_A$), the enthalpy of the reaction ($\Delta H$), and the entropy of the reaction ($\Delta S$). These values were used to calculate the dissociation constant ($K_d$) which is the reciprocal of $K_A$, and the Gibbs free energy of the reaction ($\Delta G$), which is related to the $K_A$, $\Delta H$, and $\Delta S$ by the following equations: $\Delta G=-RT$ (ln $(K_A))=\Delta H-T\Delta S$ (Levine, *Physical Chemistry*, ($2^{nd}$ ed.), McGraw-Hill Co., (1983), p. 125).

The sample cell was cleaned between injections by washing extensively with PBS, $H_2O$, and again with PBS. After multiple experiments (typically 6-8), the sample cell and syringe were more extensively cleaned using manufacturer's recommendations with a detergent solution heated to 50° C., followed by extensive washing with $H_2O$, methanol, $H_2O$, and finally PBS. Blank injections of buffer into buffer were then performed to establish sufficient cleaning and reproducible background before carrying out additional BACE-peptide experiments.

Results

Figure 2:
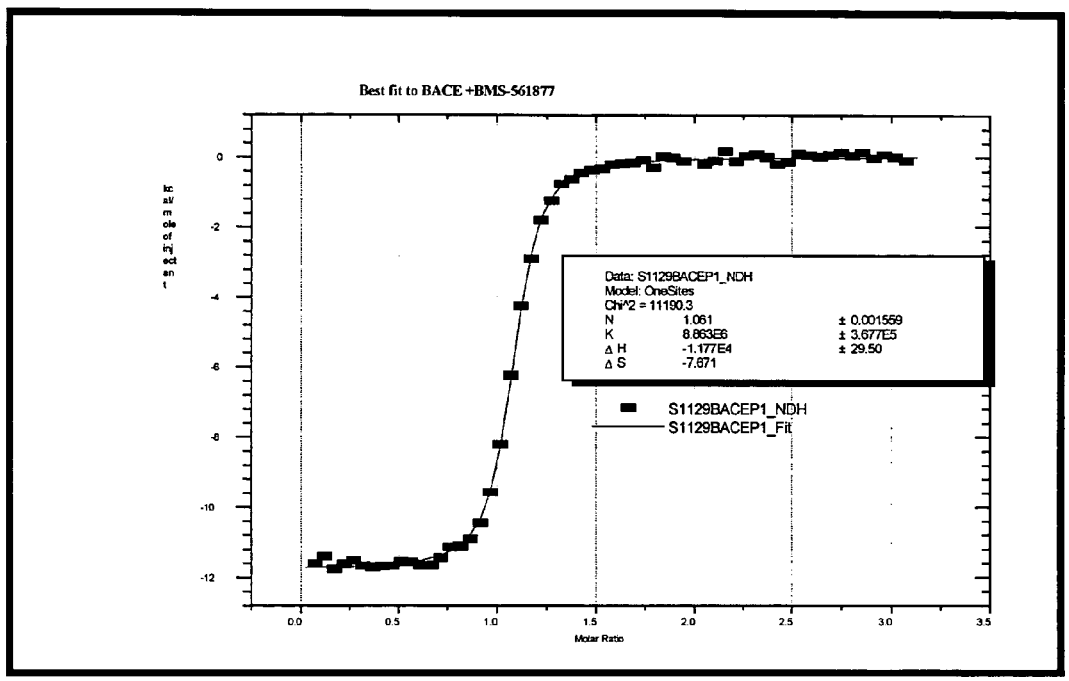
FIG. 2 shows isothermal calorimetry data quantitatively determining the binding affinity of peptide ALYPYFLPISAK (SEQ ID NO:20) to BACE at 25° C. in Dulbecco's PBS wherein the parameters were $K_A=8.86\times10^6$ $M^{-1}$; $K_d=113$ nM; n=1.06; and $\Delta H=-11.8$ kcal/mol.

Titrations with peptides NLTTYPYFIPLP (SEQ ID NO:19) and ALYPYPLPISAK (SEQ ID NO:20) into BACE demonstrated saturable 1:1 binding in Dulbecco's PBS, pH 7.1 at 25° C. (below, FIGS. 1-2). The binding constants were determined to be $K_d=61$ nM for NLTTYPYFIPLP (SEQ ID NO:19) and $K_d=113$ nM for ALYPYPLPISAK (SEQ ID NO:20).

Figure 3:
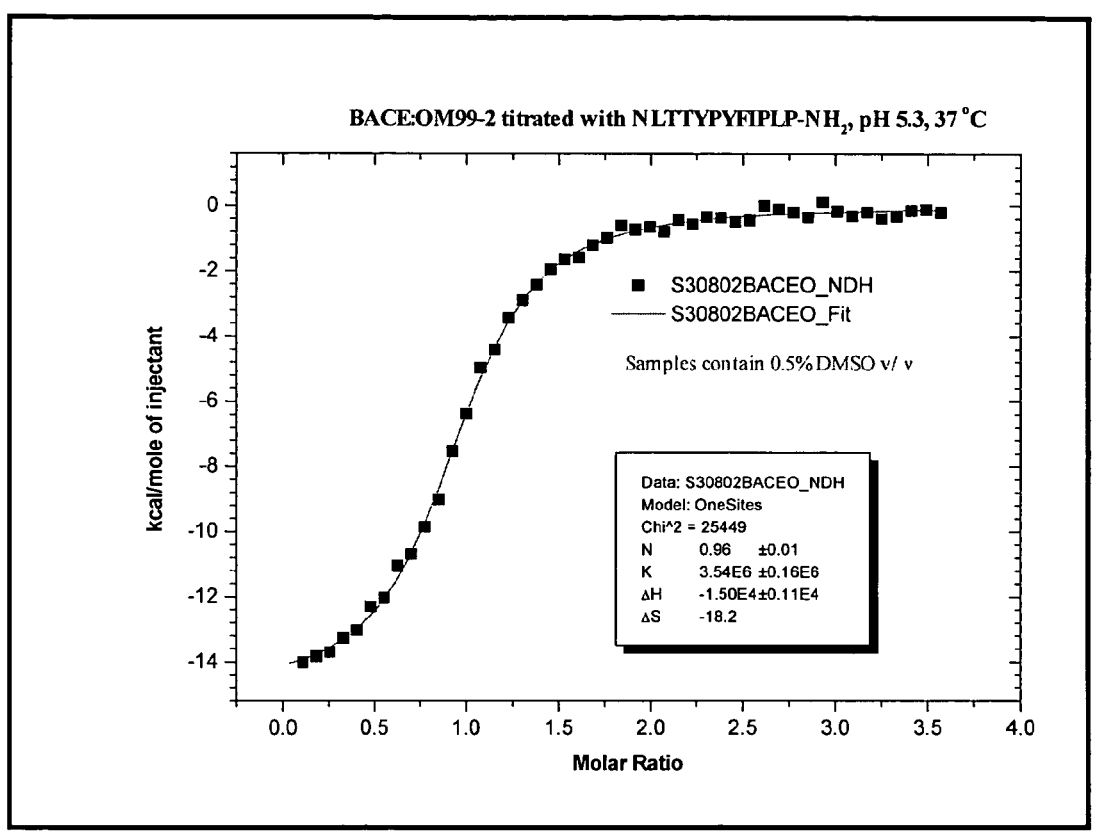
FIG. 3 shows integrated isothermal calorimetry data quantitatively determining the binding affinities of BACE-OM99-2 titrated with peptide NLTTYPYFIPLP (SEQ ID NO:19) in pH 5.3 buffer at 37° C.

Further experiments were carried out with BACE at pH 5.3 and 37° C. with NLTTYPYFIPLP (SEQ ID NO:19) to investigate the binding of this peptide under catalytically active conditions in both the absence and presence of the active site inhibitor peptide OM99-2. Representative integrated data fitted to a single site model are given below in FIG. 3 for the experiment in which a 10-fold excess of OM99-2 was first added to BACE, and the complex was then titrated with NLTTYPYFIPLP (SEQ ID NO:19), at pH 5.3, 37° C. The determined thermodynamic parameters for the complete sets of experiments are given in Table 3, and all experiments showed saturable binding and excellent fits to a single site model.

TABLE 3

Calculated and Fitted Data for Four Experiments with BACE, OM99-2, and Peptide #1, Conducted at pH 5.3, 37° C.

| Sample Cell Contents | Titrant (syringe) | ΔG (kcal/mol) | T(dS) (kcal/mol) | ΔH (kcal/mol) | $K_d$ (nM) | Stoichiometry (mole:mole) |
|---|---|---|---|---|---|---|
| CHO BACE | Peptide #1* | −9.1 | −6.8 | −15.9 | 380 | 0.93:1.00 |
| CHO BACE: OM99-2 | Peptide #1 | −9.3 | −5.7 | −15.0 | 280 | 0.96:1.00 |
| CHO BACE | OM99-2 | −11.9 | −5.3 | −17.2 | 4 | 1.01:1.00 |
| CHO BACE: Peptide #1 | OM99-2 | −12.1 | −4.0 | −16.1 | 3 | 1.03:1.00 |

*Peptide #1 is NLTTYPYFIPLP (SEQ ID NO: 19)

These experiments demonstrated that binding of peptide NLTTYPYFIPLP (SEQ ID NO:19), and OM99-2 to BACE were not mutually exclusive, and that the binding was not strongly coupled, as shown below in Scheme 1.

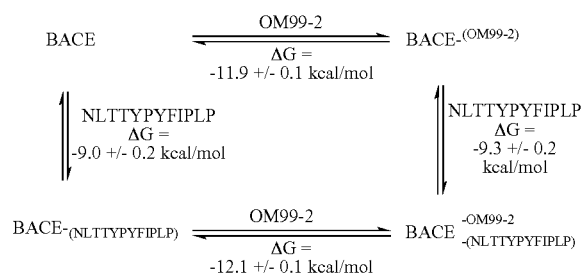

Scheme 1
Model for Thermodynamic Cycle of BACE Binding Active Site Inhibitor OM99-2 and Peptide #1: NLTTYPYFIPLP (SEQ ID NO:19), at Different Sites, and Associated Gibbs Free Energy Changes (ΔG)

Example 4

Fluorescently Labeled EBPs Binding to BACE Assay

An assay to evaluate the binding of BACE to EBPs labeled with a fluorescent molecule (for example, but not limited to Alexa488) was developed. This assay uses the catalytic domain of human BACE expressed in a CHO cell line (according to Example 3) and labeled EBPs such as Molecule X shown in FIG. 4. The change in fluorescent anisotropy of the EBP peptide upon binding to BACE is monitored.

Peptides were dissolved in 100% DMSO (dimethyl sulfoxide) at 10 mM concentration, and then diluted 10-fold into deionized water. The concentration of the labeled peptides was determined by their absorbance at 495 nm ($\epsilon$=71000 cm$^{-1}$M$^{-1}$). The concentration of selected unlabeled peptides was determined by their Tyr absorbance at 276 nm ($\epsilon$=1390 cm$^{-1}$M$^{-1}$ per Tyr residue).

The binding was carried out at pH 7.1 (PBS buffer) and pH 4.5 (50 mM acetate buffer) in the presence of 1% DMSO. Fluorescence anisotropy was measured at 25° C. in an AVIV fluorometer. The excitation and emission wavelengths were set to 495 and 519 nm, respectively. The excitation and emission slit width were 4 and 10 nm, respectively. A concentrated BACE stock was used to titrate a 300 μl solution of 10 nM labeled EBP. The final BACE concentration ranges from 10 to 5000 nM. After the addition of BACE, the solution was mixed for 10 times with a pipettor. The fluorescence anisotropy was averaged over a 5 minute period.

Figure 5:
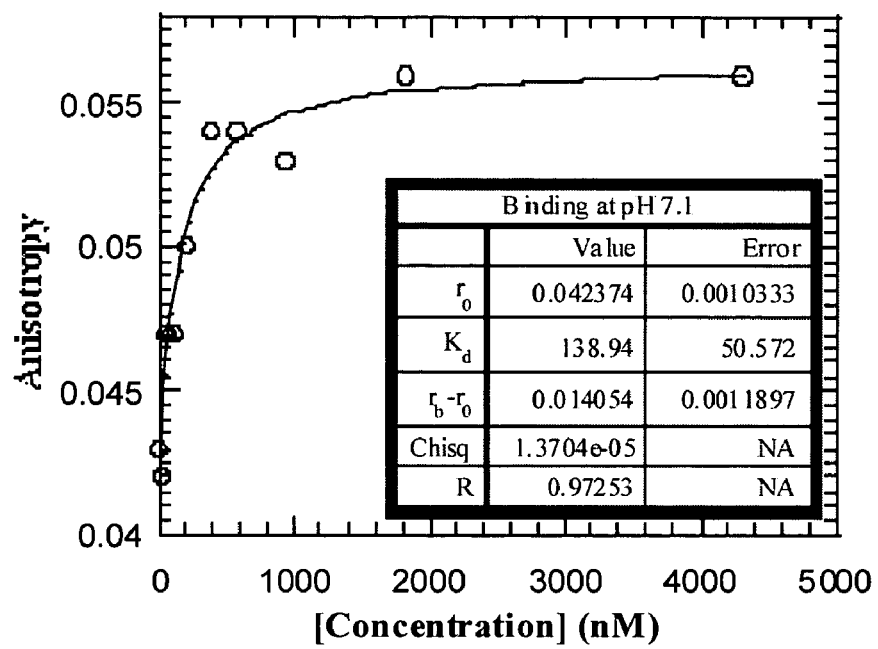
FIG. 5 shows fluorescence anisotropy data demonstrating that labeled EBP Molecule X binds to BACE at pH 7.1 (upper panel) and pH 4.5 (lower panel). The solid lines represent fitting the data to a 1:1 binding model.
Figure 5:
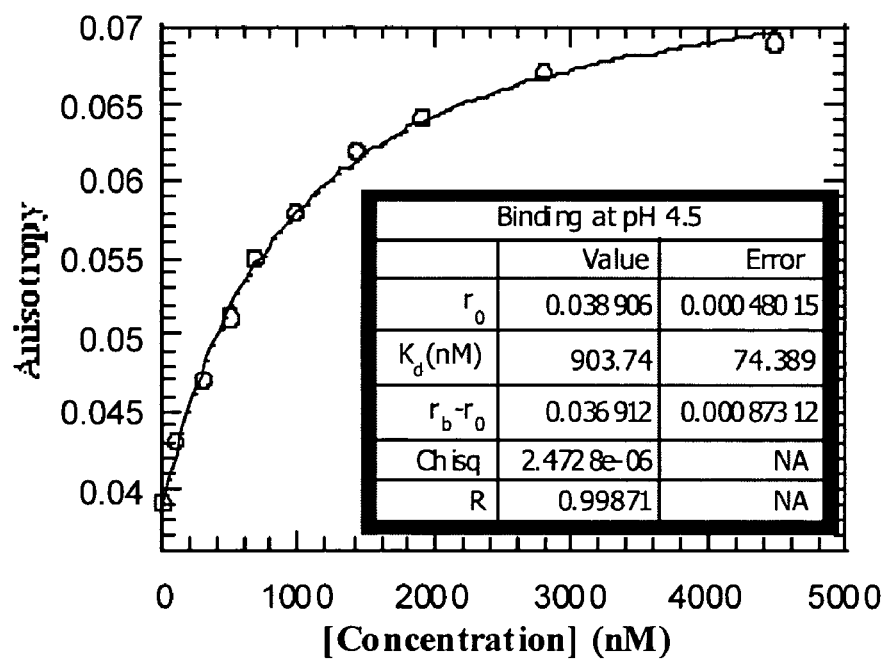

The change in anisotropy was plotted against the BACE concentration (see, for example, FIG. 5). The $K_d$ of the labeled EBP as well as the initial ($r_0$) and final anisotropy ($r_b$) of the labeled EBP were calculated from curve fitting using the program Kaleidagraph. The equation used to fit the binding data is identical to equation 1 in Lai et al., (2000) Arch. Biochem. Biophys. 381:278-284.

Example 5

Competitive Binding Assay

The competitive binding assay was carried out at pH 7.1 (PBS buffer) or pH 4.5 (50 mM acetate buffer). The fluorescence anisotropy was measured at 25° C. in an AVIV fluorometer. The excitation and emission wavelengths were set to 495 and 519 nm, respectively. The excitation and emission slit widths were 4 and 10 nm, respectively.

Labeled EBP (Molecule X) at 10 nM was mixed with BACE at a concentration equal to the $K_d$. The initial anisotropy value was measured. A concentrated unlabeled peptide or compound stock was titrated into the above solution of EBP and BACE. The final concentration of unlabeled peptide or compound ranges from 20 to 20000 nM. After each addition, the solution was mixed for 10 times with a pipettor. The fluorescence anisotropy was averaged over a 5 minute period.

Figure 6:
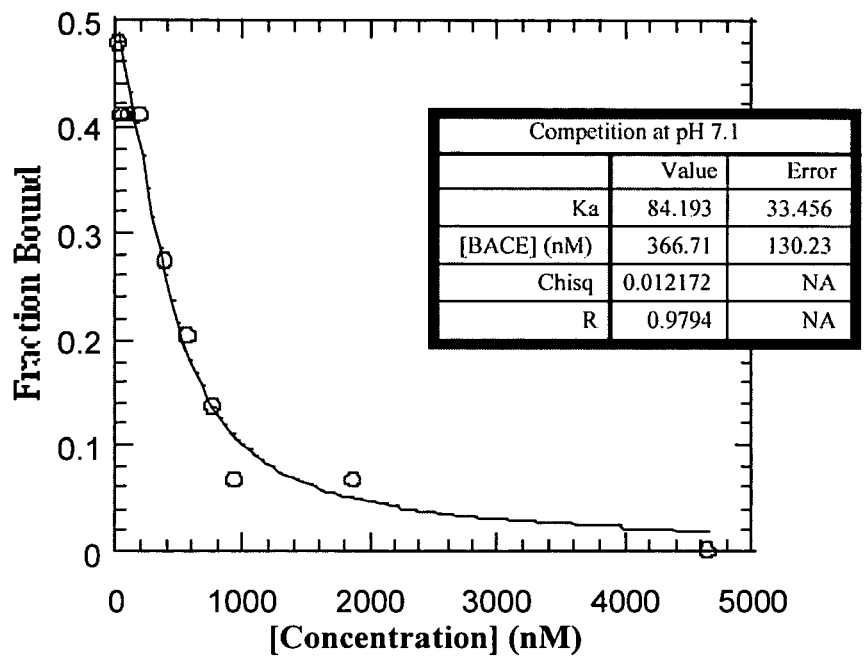
FIG. 6 shows that BMS-561871, peptide NLTTYPYFIPLP (SEQ ID NO:19) (Molecule X without the Alexa488 label) competes with the binding of Molecule X at pH 7.1 (upper panel) and pH 4.5 (lower panel), as monitored by fluorescence anisotropy.
Figure 6:
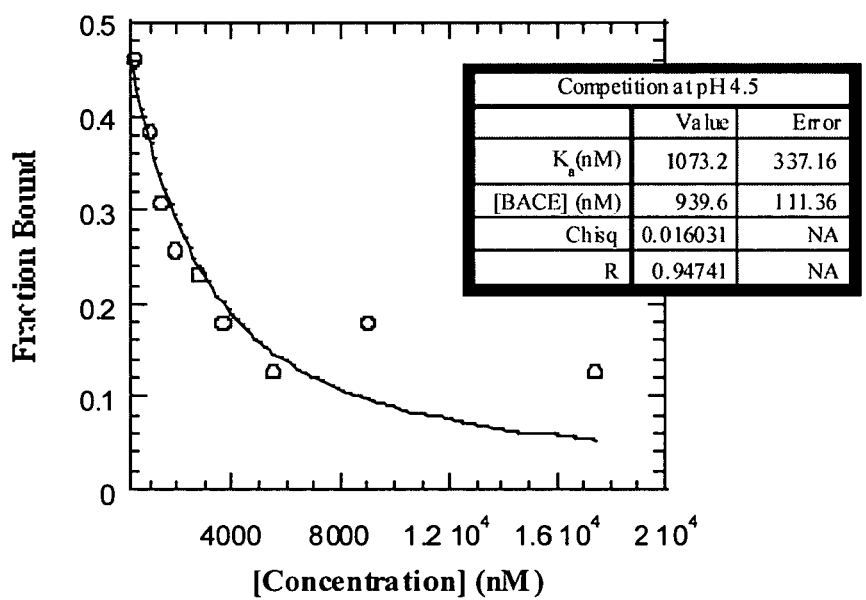

The change in anisotropy was converted to fractional occupancy based on the $r_0$ and $r_b$ obtained from the binding assay. The fractional occupancy was then plotted against the concentration of the competing peptide or compound. (see, for example, FIG. 6) The $K_d$ of the competing ligand was calculated from curve fitting using the program KALEIDAGRAPH™ (Synergy Software, Reading, Pa.). The equation used to fit the competition data is identical to equation 4 in Lai et al., (2000) Arch. Biochem. Biophys. 381:278-284.

Example 6

Binding of Labeled EBP (Molecule X) to BACE at pH 7.1 and pH 4.5

Binding of a labeled EBP (Molecule X, FIG. 4) to BACE was carried out at pH 7.1 and pH 4.5. By fitting of the data to a 1:1 binding model, the binding constants were determined to be 139 and 904 nM at pH 7.1 and pH 4.5, respectively.

Example 7

Determination of Binding Affinity of Unlabeled EBP using the Competition Assay

The binding affinity of peptide NLTTYPYFIPLP (SEQ ID NO:19) (unlabeled Molecule X) was determined using the competition assay as described in Example 6. The binding constants were 84 and 1073 nM at pH 7.1 and pH 4.5, respectively. The ability of unlabeled EBP to displace Molecule X from binding to BACE suggests that the labeled and unlabeled peptides bind to BACE at the same exosite. The binding constants of this EBP with and without Alexa488 label at essentially the same at both pHs, indicating that the presence of the Alexa488 label does not affect the binding interactions of the EBP to BACE. The binding constant at pH 7.1, determined by the fluorescent anisotropy, is consistent with the ITC result (61 nM) of Example 3. At pHs where BACE will be catalytically active, the binding of the EBP NLTTYPYFIPLP (SEQ ID NO:19) is weaker (1073 nM at pH 4.5 by fluorescence anisotropy and 380 nM at pH 5.3 by ITC). Unless otherwise specified, subsequent binding and competition experiments were carried out at pH 4.5, the pH optimum of the proteolytic activity of BACE.

Example 8

Figure 7:
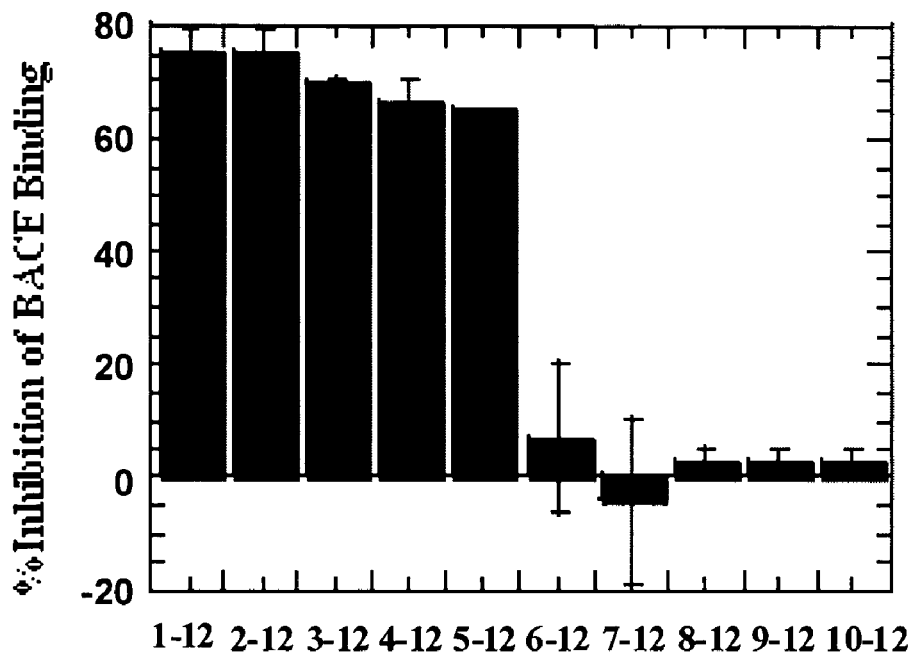
FIG. 7 shows inhibition of the binding of Molecule X to BACE by a collection of N-terminally (upper panel) and C-terminally (lower panel) truncated unlabeled peptides monitored by fluorescence anisotropy. The numbered identifiers on the X-axis refer to the amino acid composition with respect to BMS-561871.
Figure 7:
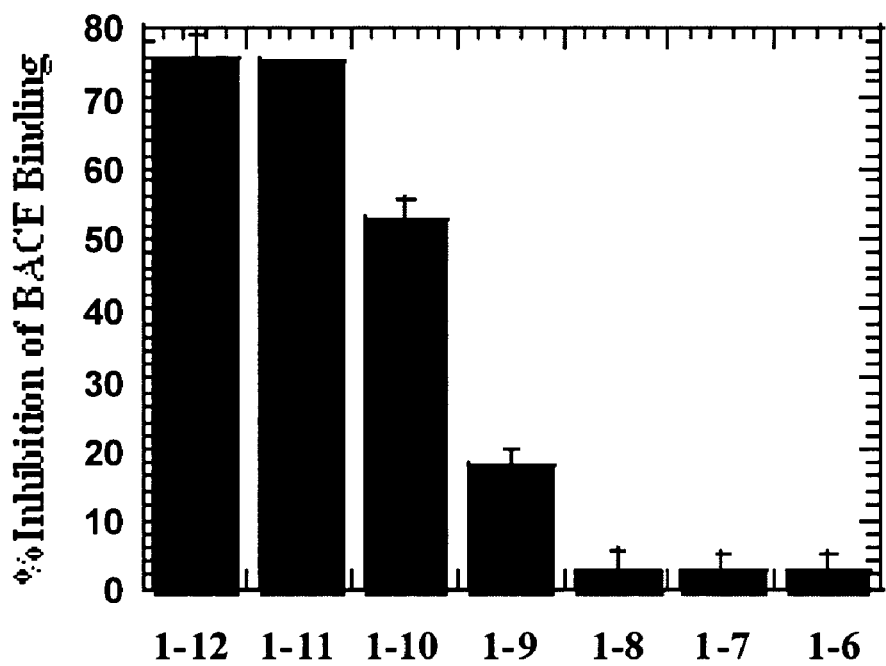

Screening of Truncated Peptides to Define the Minimal Length Requirement for Binding A collection of truncated peptides (from N-, from C-, and from both N- and C-termini of peptide NLTTYPYFIPLP (SEQ ID NO:19)) was screened in the competition assay described above in Example 6 with slight modification. Molecule X was used as the labeled EBP ($K_d$=1.0 µM at pH 4.5). The truncated unlabeled peptides were screened at a single concentration of 10 µM at pH 4.5. The anisotropy values detected with Molecule X in the absence of inhibitor, i.e., truncated unlabeled peptide ($r_a$) and in the presence of the inhibitor ($r_b$) and the labeled peptide alone ($r_0$) were used to calculate the percent of inhibition: 100 $(r_a-r_b)/(r_a-r_0)$. The percent of inhibition was compared among the truncated peptides. It was determined that the N-terminal 4 residues and the C-terminal residue in peptide NLTTYPYFIPLP (SEQ ID NO:19) were not critical in binding (FIG. 7, upper and lower panels). Therefore, it was determined that the minimal length desired for binding is a 7-mer peptide. A preferred 7-mer BACE exosite binding peptide was identified having the sequence of YPYFIPL (SEQ ID NO:10), corresponding to amino acids 5-11 in the original NLTTYPYFIPLP (SEQ ID NO:19) peptide.

In addition to Molecules X, Yn, and Z, the following BACE exosite binding peptides were identified:

| Compound Number | Sequence | Amino Acid Composition | |
|---|---|---|---|
| BMS-561871 | 1-12 | NLTTYPYFIPLP | (SEQ ID NO:19) |
| BMS-593925 | 5-11 | YPYFIPL | (SEQ ID NO:10) |
| BMS-590022 | 2-12 | LTTYPYFIPLP | (SEQ ID NO:44) |

-continued

| Compound Number | Sequence | Amino Acid Composition | |
|---|---|---|---|
| BMS-590023 | 3-12 | TTYPYFIPLP | (SEQ ID NO:45) |
| BMS-590024 | 4-12 | TYPYFIPLP | (SEQ ID NO:46) |
| BMS-590008 | 5-12 | YPYFIPLP | (SEQ ID NO:47) |
| BMS-590014 | 1-11 | NLTTYPYFIPL | (SEQ ID NO:48) |
| BMS-599191 | 5-11[a] | YPYFIAL | (SEQ ID NO:49) |
| BMS-599192 | 5-11[a] | YPYFIPA | (SEQ ID NO:50) |
| BMS-599195 | 5-11[b] | YPBFIPL | (SEQ ID NO:51) |
| BMS-599199 | 5-11[b] | YPYFIPB | (SEQ ID NO:52) |
| BMS-607641 | 5-11[d] | YPYFIPB-Alexa488 | (SEQ ID NO:108) |
| BMS-607649 | 5-11[d] | YPBFIPL-Alexa488 | (SEQ ID NO:109) |

[a] Peptides corresponding to the BMS-593925 sequence with an Ala mutation.
[b] Peptides corresponding to the BMS-593925 sequence with a Bpa mutation.
[c] Peptide containing the same amino acid as BMS-593925, but the sequence is scrambled.
[d] Two peptides corresponding to the BMS-593925 sequence with a Bpa mutation and Alexa488 attached to the C-terminus.

Example 9

Figure 8:
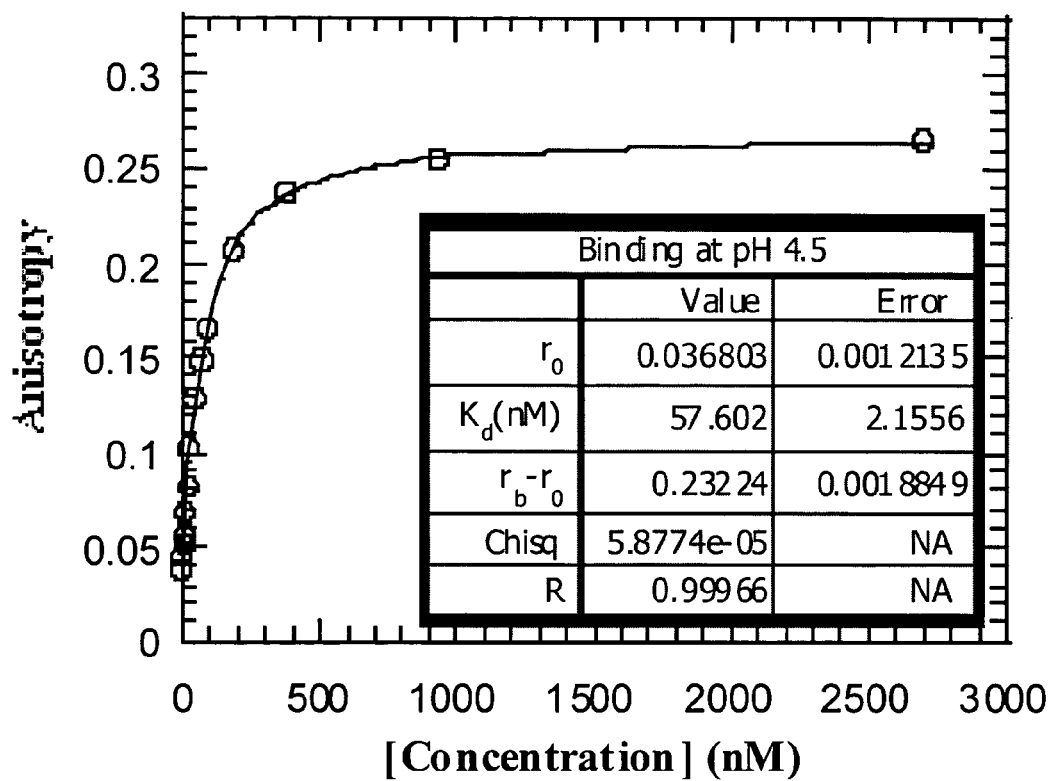
FIG. 8 shows the binding of Molecule Y1 to BACE at pH 4.5 by fluorescence anisotropy. The solid line represents fitting the data to a 1:1 binding model.

Characterization of EBPs Labeled at Different Positions and with Linkers of Different Lengths A comparison of EBPs labeled with Alexa488 at different positions (Molecules X, Y1, Z) was performed using the above binding assay. It is preferred that the labeled EBP exhibit tight binding affinity and a high signal to background ratio (i.e., ratio of the anisotropy upon binding to BACE and the anisotropy of the free EBP peptide). The binding constants of Molecules X, Y1, and Z were determined to be 903, 58, and 6430 nM, respectively. Molecule Y1 not only exhibits the tightest affinity for BACE, but also the best signal to background ratio. An example of Molecule Y1 binding to BACE is shown in FIG. 8.

Figure 4:
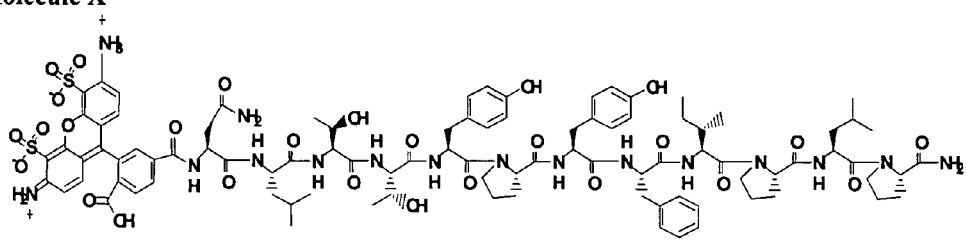
FIG. 4 shows EBPs labeled with the fluorescent group Alexa488 at different positions (Molecules X, Yn and Z of Example 9) and with linkers of different lengths (Yn, wherein n=1-4).
Figure 4:
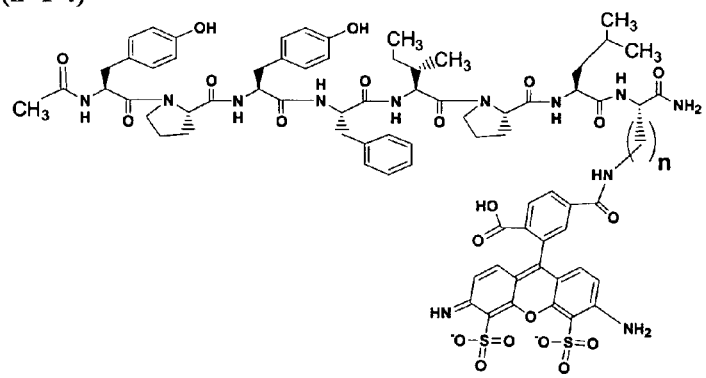
Figure 4:
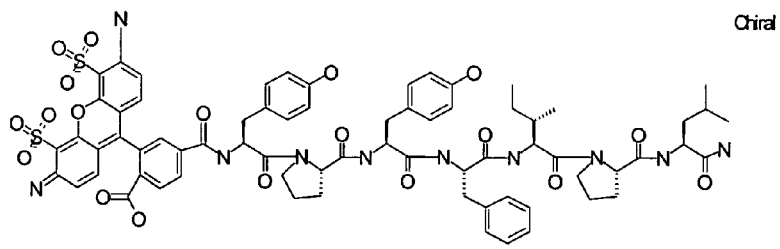

Analogs of Molecule Y1 were prepared with different length of linkers (FIG. 4). The binding constants of Y1, Y2, Y3, and Y4 were 57, 92, 48, 62 nM, respectively. The lack of change in the affinity of Molecules Yn (where n=1-4) for BACE indicates that the length of linker between Alexa488 and the peptide does not affect the strength of binding interaction.

Example 10

Binding of Molecule Y1 can be Displaced by Unlabeled EBP

Figure 9:
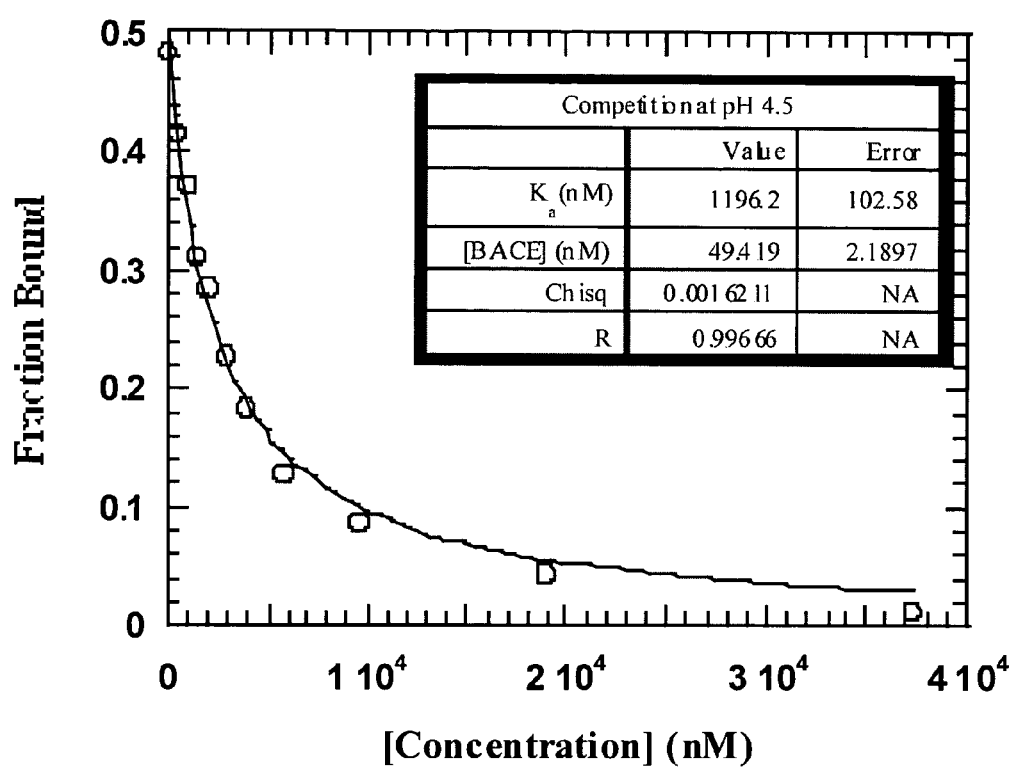
FIG. 9 shows that BMS-593925, peptide YPYFIPL (SEQ ID NO:10) (Molecule Y1 without the Alexa488 label) competes with the binding of Molecule Y1 at pH 4.5 monitored by fluorescence anisotropy.

Unlabeled EBP corresponding to Molecule Y1 (BMS-593925, YPYFIPL (SEQ ID NO:10)) was used in the competition assay to displace Molecule Y1 from binding to BACE at pH 4.5 (see FIG. 9). The unlabeled EBP was found to bind to BACE with a $K_d$ of 1197 nM. This demonstrates that although the presence of the C-terminal Alexa488 on Molecule Y1 increased the affinity of Y1 for BACE, it still

Example 11

Figure 10:
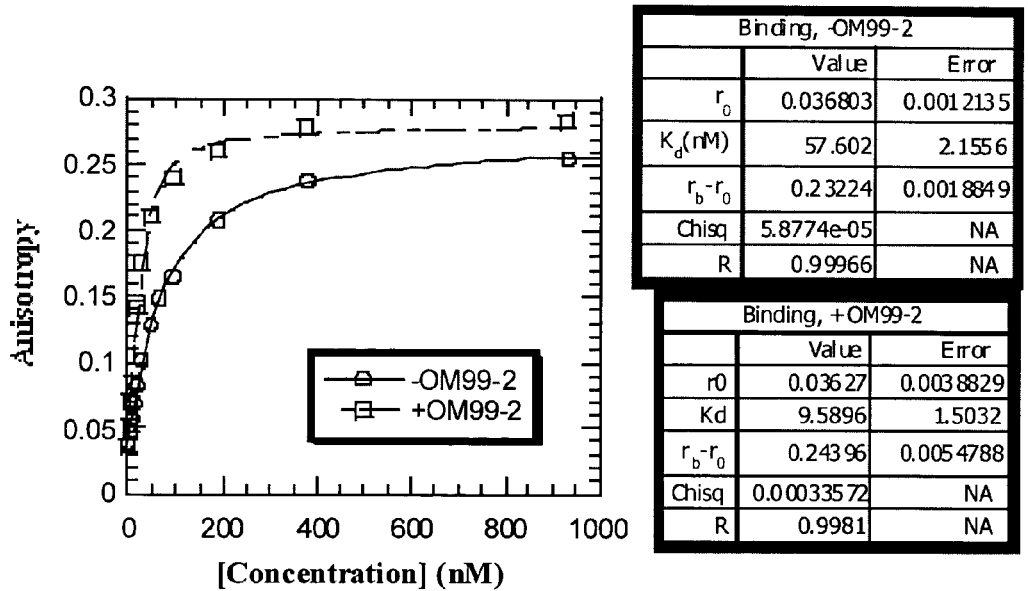
FIG. 10 shows the fluorescence anisotropy measurement of Molecule Y1 binding to BACE both in the absence (circles) and in the presence (squares) of OM99-2, an active site-directed inhibitor of BACE, suggesting that Molecule Y1 does not bind to BACE at the active site.

Binding of a Labeled EBP to BACE in the Presence of an Active Site Inhibitor The binding assay described herein above was used to determine the binding affinity of Molecule Y1 to BACE in the presence of 10 µM OM99-2, a known BACE inhibitor that binds to BACE at the active site with a $K_i$ of 2 nM (FIG. 10). Before the addition of BACE, a concentrated stock (1 mM in 100% DMSO) of OM99-2 was mixed with the 300 µl solution of 10 nM labeled EBP (molecule Y1) to a final OM99-2 concentration of 10 µM. BACE was then titrated into this mixture of OM99-2 and labeled EBP as described above. It was found the EBP (molecule Y1) binds to BACE with somewhat enhanced affinity (5-fold) in the presence of 10 µM OM99-2. This demonstrates that the EBP does not bind to BACE at the same site as OM99-2, i.e., it binds at an exosite away from the active site. The binding of OM99-2 at the active site may have a positively cooperative effect on the EBP binding.

Example 12

Binding of Labeled EBP to BACE Purified from E. coli Cells

Binding of Molecule Y1 to the catalytic domain of BACE purified from E. coli cells was carried out to determine the effect of glycosylation on the EBP binding. It is known that proteins purified from E. coli do not have glycosylation. The binding affinity of E. coli expressed human BACE for EBPs was found to be the same as that of human BACE purified from CHO cells, indicating that the EBPs are indeed binding to the BACE protein, rather than the sugar groups.

Example 13

Determination of the Contribution of Each Amino Acid in EBP by Ala Scan and Bpa Scan A collection of mutated peptides base on peptide YPY-FIPL (SEQ ID NO:10) was screened using the competition assay described in Example 9.

Figure 11:
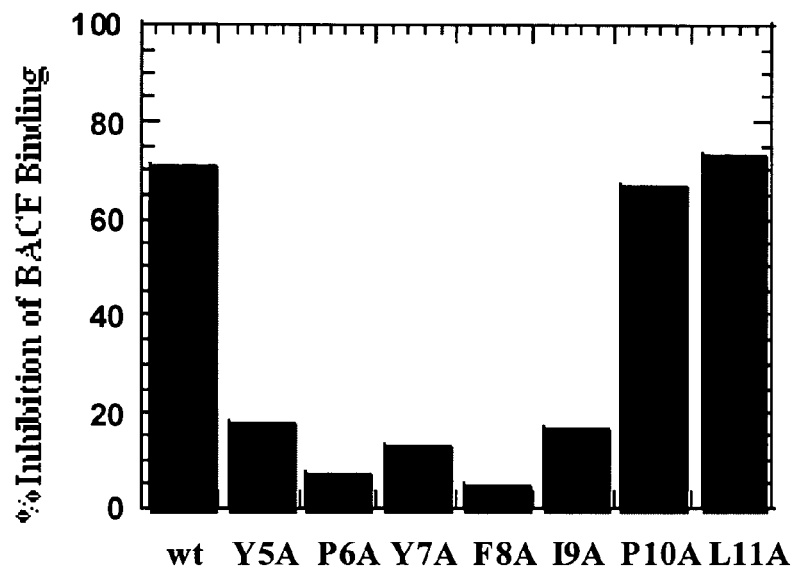
FIG. 11 shows the inhibition of the binding of Molecule Y1 to BACE by a collection of mutated peptides based on peptide YPYFIPL (SEQ ID NO:10) (wt sequence, corresponding to 5-11 in the original NLTTYPYFIPLP peptide; SEQ ID NO:19): Upper panel: Peptides with a mutation to Ala at the indicated position. Lower panel: Peptides with a mutation to benzophenone (Bpa or B) at the indicated position. N—B and C—B represent peptides that have the Bpa group attached to the N- and C-terminus, respectively. Peptides P6B, I9B, and C—B (indicated by asterisks in the figure) have limited solubility, therefore, the inhibition of binding between Molecule B1 and BACE is under determined in these cases.
Figure 11:
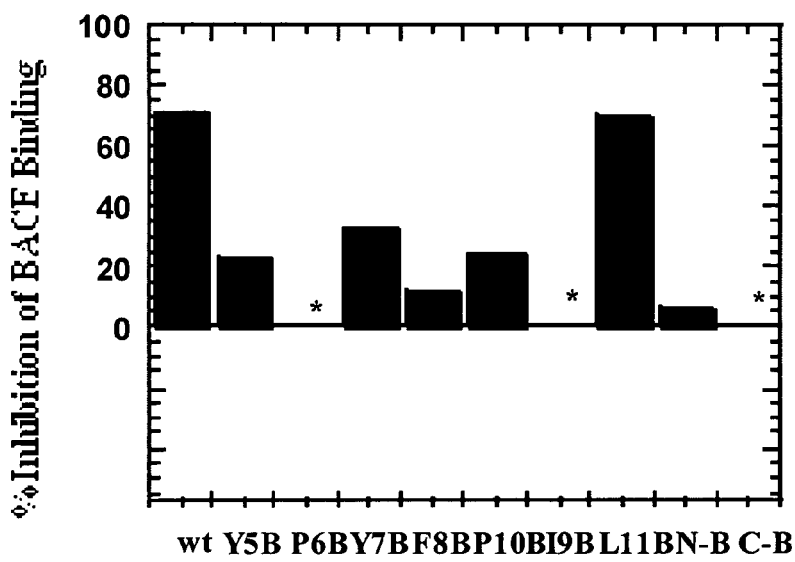

The results of the Ala scan shown in FIG. 11 (upper panel) suggests that while the last two amino acids (PL) are not critical for the binding interaction, the other five amino acids (YPYFI; SEQ ID NO:2) all play an important role in the interaction of the EBP with BACE.

The result of the scan of benzophenone-containing peptides (see FIG. 11, lower panel) suggests that Leu-11 can be replaced with a benzophenone (Bpa) group. Tyr-7 accommodates a Bpa substitution better than most other positions, but not as well as Leu-11.

Example 14

Photo-Crosslinking of Bpa Containing EBPs to BACE

Figure 12:
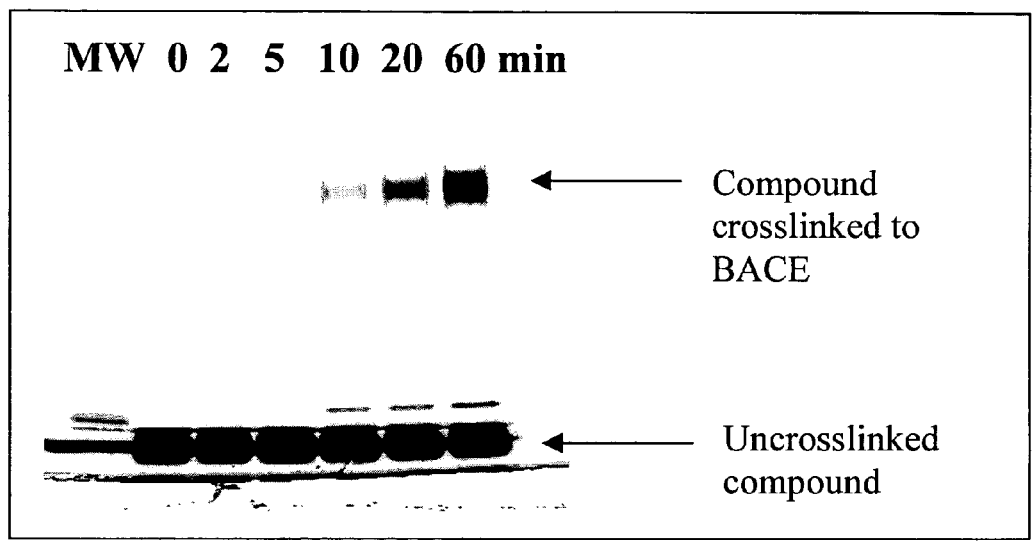
FIG. 12 shows a fluoroimage (excitation at 488 nm, emission at 530 nm) of the time course of the photocrosslinking of BACE (2 μM) to a Bpa-containing EBP, BMS-607641, with the sequence of YPYFIPB-Alexa488 (2 μM) (SEQ ID NO:108) in the presence of 100 μM of a scrambled peptide (BMS-599271, LYPPYIF; SEQ ID NO:53) at 4° C.

Two EBPs containing a Bpa substitution as well as an Alexa488 group attached at the C-terminus (YPYFIPB-Alexa488 (SEQ ID NO:108) and YPBFIPL-Alexa488 (SEQ ID NO:109); where B indicates a benzophenone group) were tested for their binding to BACE. They were both found to bind to BACE reversibly with affinities around 100 nM in the absence of UV light. Both peptides were used to covalently crosslink to BACE upon UV irradiation at 360 nm. The crosslinking reaction was carried out at various temperatures in the presence of 2 µM BACE, various amounts of EBP containing the Bpa group, as well as 100 µM of a scrambled peptide with the sequence of LYPPYIF (SEQ ID NO:53) that does not bind to BACE. The reaction mixture was separated by SDS-PAGE and visualized on a Fluoroimager (Molecular Dynamics) with an excitation of 488 nm and an emission of 530 nm. FIG. 12 shows a typical time course of the crosslinking reaction of BMS-607641. The Bpa containing EBPs can be covalently crosslinked to BACE and thus serve as tools for the determination of the structure of the exosite on BACE.

Example 15

Assay for Identifying BACE Exosite Binding Compounds

Compounds that bind to BACE at the exosite can be discovered using the competition assay described in Examples 5 and 9. By mixing compounds at a single concentration or varying concentrations with a fixed concentration mixture of BACE and labeled EBP, changes in the fluorescence anisotropy of the Alexa488 group are followed to determine the competition (or the lack of) of compounds for the EBP binding to BACE. To facilitate the high throughput discovery of exosite binding compounds of BACE, the assay is carried out in a 96, 384, or 1536 well format.

Example 16

Molecule Y3 Inhibits the Proteolytic Activity of BACE

Molecule Y3 was tested in a BACE cleavage assay using the peptide MCA-EVNLDAEFK(-dnp)-COOH (SEQ ID NO:107) as a substrate. The assay was carried out essentially as described in Mallender et al., (2001) *Mol. Pharmacol.* 59:619-626 and in Marcinkeviciene et al., (2001) *J. Biol. Chem.* 276: 23790-23794. A concentration of 0.1 nM BACE was incubated with Molecule Y3 at various concentrations for 15 minutes before substrate peptide was added to a final concentration of 25 µM. The reaction was allowed to proceed for 60 minutes at 25° C. before it was stopped by boiling. The reaction mixture was separated on a C18 column using reverse phase HPLC (Waters, Milford, Mass.). The $IC_{50}$ value was calculated using the Langmuir isotherm equation (Copeland, R. A., *Enzymes: A Practical Introduction to Structure, Mechanism, and Data Analysis*, ($2^{nd}$ ed), Wiley-VCH, New York, N.Y. (2000)).

Figure 13:
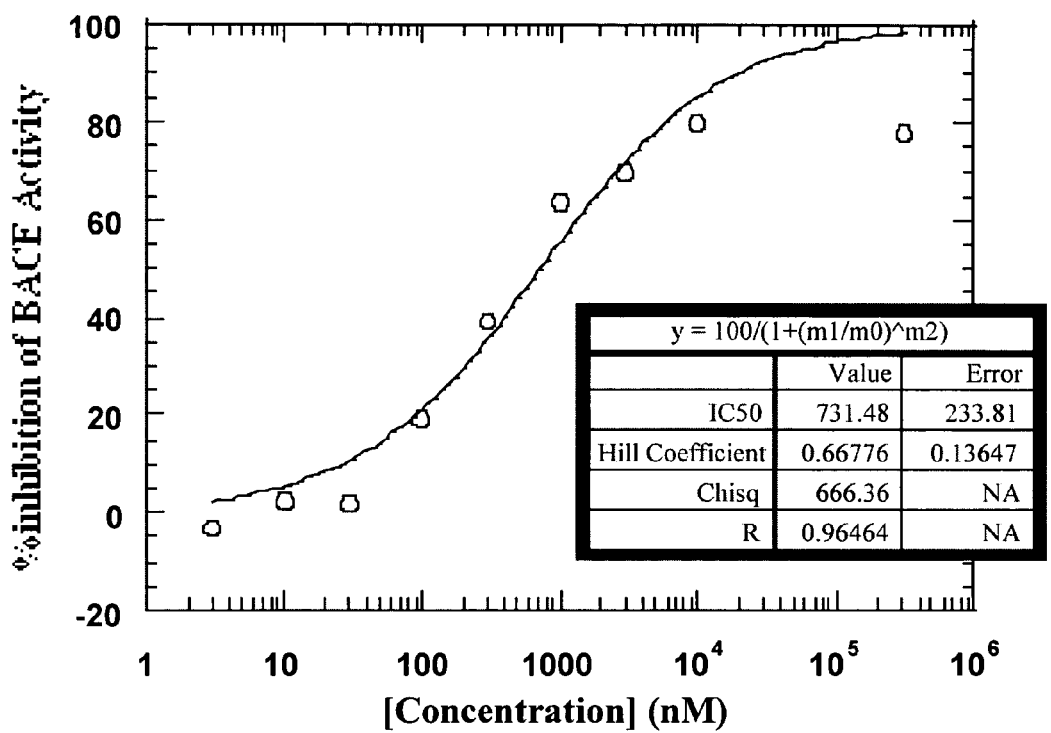
FIG. 13 shows that Molecule Y3 inhibits the proteolytic activity of BACE monitored by HPLC analysis. The solid line represents fitting of the data to the Langmuir isotherm equation (Copeland. R. A., *Enzymes: A Practical Introduction to Structure, Mechanism, and Data Analysis*, ($2^{nd}$ ed), Wiley-VCH, New York, N.Y. (2000)).

Molecule Y3 was found to inhibit the proteolytic activity of BACE with an $IC_{50}$ of 731 nM (FIG. 13), demonstrating that binding of EBPs to the exosite on BACE can indeed interfere with the catalytic activity of BACE. The inhibition by EBP may be more potent when protein substrates, containing an APP sequence, are used instead of short peptide substrate.

Example 17

Peptide Synthesis

The EBP peptides described herein were prepared using either an Applied Biosystems Inc. 433A peptide synthesizer or an Advanced Chemtech Multiple Peptide Synthesizer (MPS-396). The MPS-396 synthesizer was used to prepare several peptides simultaneously. The ABI 433A synthesizer was used to prepare individual peptides one at a time.

The syntheses of the peptide analogs described herein were also carried out either by using an Advanced Chemtech Multiple Peptide Synthesizer (MPS-396) or an Applied Biosystems Inc. peptide synthesizer. The step-wise solid phase peptide synthesis was carried out utilizing the Fmoc/t-butyl protection strategy. The amino acid derivatives used for the chain building were protected by the Fmoc group at the α-amino, and the side chain functionalities were protected by groups that are resistant to piperidine treatment, but ultimately cleavable by trifluoroacetic acid.

Example 18

Simultaneous Solid Phase Peptide Synthesis of EBP Peptides 4-(2',4'-dimethoxyphenyl-Fmoc-aminomethyl)-phenoxyacetyl-p-methyl benzhydrylamine resin (Rink amide MBHA resin; loading: 0.5 mmol/g) was loaded as a suspension in dichloromethane/DMF (60:40) into the 96-well reactor of an Advanced ChemTech MPS 396 synthesizer in volumes corresponding to 0.01-0.025 mmol (20-50 mg) of resin per reactor well. The reactor was placed on the instrument and drained. The wells were then washed with DMF (0.5-1.0 mL, 3×2 min) and subjected to the number of automated coupling cycles required to assemble the respective peptide sequences as determined by the pre-programmed sequence synthesis table. The detailed stepwise synthesis protocol used for a typical 0.01 mmol/well simultaneous synthesis of 96 compounds is described below. This protocol was adapted for the simultaneous synthesis of arrays of analogs. The general synthesis protocol is depicted in Scheme 2.

Scheme 2
Automated Synthesis of EBP Peptide Analogs

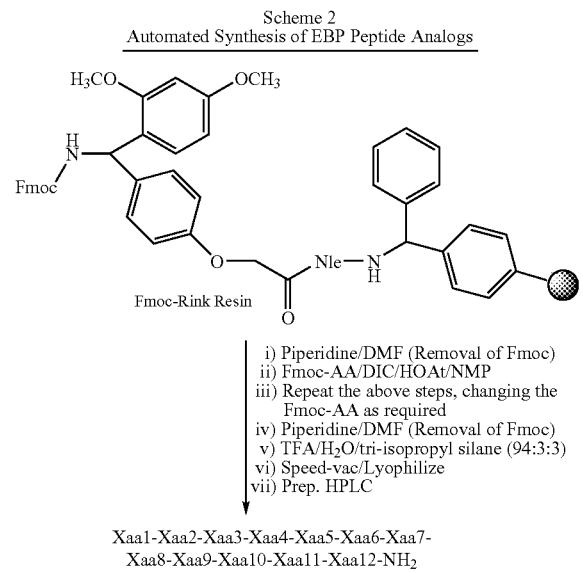

i) Piperidine/DMF (Removal of Fmoc)
ii) Fmoc-AA/DIC/HOAt/NMP
iii) Repeat the above steps, changing the Fmoc-AA as required
iv) Piperidine/DMF (Removal of Fmoc)
v) TFA/H$_2$O/tri-isopropyl silane (94:3:3)
vi) Speed-vac/Lyophilize
vii) Prep. HPLC Xaa1-Xaa2-Xaa3-Xaa4-Xaa5-Xaa6-Xaa7-Xaa8-Xaa9-Xaa10-Xaa11-Xaa12-NH$_2$ Prior to starting the synthesis, the following reagent solutions were prepared and placed on the instrument as required: 1.5 M (15%) piperidine in DMF; 0.5 M DIEA in NMP; 0.36 M DIC in NMP; 1 M (10%) acetic anhydride in DMF. The required Fmoc-protected amino acids were prepared as 0.36 M solutions in 0.36 M HOAt/NMP and placed into the appropriate positions in the 32-position amino acid rack.

Coupling of the amino acid residue was carried out by automated addition of a 0.36 M solution of the appropriate Fmoc-amino acid (0.072 mmol, 7.2 eq.) and HOAt (7.2 eq.) in NMP (0.2 mL) to all relevant wells. This was followed by addition of a 0.36 M solution of DIC (0.072 mmol, 7.2 eq.) in NMP (0.2 mL). The coupling was allowed to proceed for 2 hrs. After reactor draining by nitrogen pressure (3-5 psi) and washing the wells with NMP (1×0.5 mL), the coupling was repeated as described above. At the end of the coupling cycle, the wells were treated with 1M acetic anhydride in DMF (1×0.5 mL, 30 min.) and finally washed with DMF (3×0.5 mL).

An identical coupling protocol was repeated additional times in order to complete the sequence assembly of the desired peptide analogs.

Finally, the Fmoc group was removed with 20% piperidine in DMF as described above, and the peptidyl-resins were washed with DMF (4×0.5 mL) and DCM (4×0.5 mL). They were then dried on the reactor block by applying a constant pressure of nitrogen gas (5 psi) for 10-15 min.

Cleavage/Deprotection

The desired peptides were cleaved/deprotected from their respective peptidyl-resins by treatment with a TFA cleavage mixture as follows. A solution of TFA/water/tri-isopropylsilane (94:3:3) (1.0 mL) was added to each well in the reactor block, which was then vortexed for 2 hrs. The TFA solutions from the wells were collected by positive pressure into pre-tared vials located in a matching 96-vial block on the bottom of the reactor. The resins in the wells were rinsed twice with an additional 0.5 mL of TFA cocktail and the rinses were combined with the solutions in the vials. These were dried in a SpeedVac™ (Savant) to yield the crude peptides, typically in >100% yields (20-40 mgs). The crude peptides were either washed with ether or more frequently re-dissolved directly in 2 mL of DMSO or 50% aqueous acetic acid for purification by preparative HPLC as follows.

Preparative HPLC Purification of the Crude Peptides

Preparative HPLC was carried out either on a Waters Model 4000 or a Shimadzu Model LC-8A liquid chromatograph. Each solution of crude peptide was injected into a YMC S5 ODS (20×100 mm) column and eluted using a linear gradient of MeCN in water, both buffered with 0.1% TFA. The desired product eluted well separated from impurities, typically after 8-10 min., and was collected in a single 10-15 mL fraction on a fraction collector. The desired peptides were obtained as amorphous white powders by lyophilization of their HPLC fractions.

HPLC Analysis of the Purified Peptides

After purification by preparative HPLC as described above, each peptide was analyzed by analytical RP-HPLC on a Shimadzu LC-10AD or LC-10AT analytical HPLC system consisting of: a SCL-10A system controller, a SIL-10A auto-injector, a SPD10AV or SPD-M6A UV/VIS detector, or a SPD-M10A diode array detector. A YMC ODS S3 (4.6×50 mm) column was used and elution was performed using a linear gradient of MeCN in water, both buffered with 0.1% TFA. Mobile phase A: 0.1% TFA/water; mobile phase B: 0.1% TFA/acetonitrile. The purity was typically >90%.

Characterization by Mass Spectrometry

Each peptide was characterized by electrospray mass spectrometry (ES-MS) either in flow injection or LC/MS mode. Finnigan SSQ7000 single quadrupole mass spectrometers (ThermoFinnigan, San Jose, Calif.) were used in all analyses in positive and negative ion electrospray mode. Full scan data was acquired over the mass range of 300 to 2200 amu for a scan time of 1.0 second. The quadrupole was operated at unit resolution. For flow injection analyses, the mass spectrometer was interfaced to a Waters 616 HPLC pump (Waters Corp., Milford, Mass.) and equipped with an HTS PAL autosampler (CTC Analytics, Zwingen, Switzerland). Samples were injected into a mobile phase containing 50:50 water:acetonitrile with 0.1% ammonium hydroxide. The flow rate for the analyses was 0.42 mL/min. and the injection volume 6 µL. A ThermoSeparations Constametric 3500 liquid chromatograph (ThermoSeparation Products, San Jose, Calif.) and HTS PAL autosampler were used for LC/MS analyses. Chromatographic separations were achieved employing a Luna $C_{18}$, 5 micron column, 2×30 mm (Phenomenex, Torrance, Calif.). The flow rate for the analyses was 1.0 mL/min and column effluent was split, so that the flow into the electrospray interface was 400 µL/min. A linear gradient from 0% to 100% B in A over 4 minutes was run, where mobile phase A was 98:2 water:acetonitrile with 10 mM ammonium acetate and mobile phase B was 10:90 water:acetonitrile with 10 mM ammonium acetate. The UV response was monitored at 220 nm. The samples were dissolved in 200 µL 50:50 $H_2O$:MeCN (0.05% TFA). The injection volume was 5 µl.

In all cases, the experimentally measured molecular weight was within 0.5 Daltons of the calculated monoisotopic molecular weight.

Example 19

Solid Phase Synthesis of EBP Peptide Analogs using an Applied Biosystems Model 431A Peptide Synthesizer Following is the general description for the solid phase synthesis of typical EBP peptide analogs, using an upgraded Applied Biosystems Model 433A peptide synthesizer. The upgraded hardware and software of the synthesizer enabled conductivity monitoring of the Fmoc deprotection step with feedback control of coupling. The protocols allowed a range of synthesis scale from 0.05 to 0.25 mmol.

4-(2',4'-dimethoxyphenyl-Fmoc-aminomethyl)-phenoxy-acetyl-p-methyl benzhydrylamine resin (Rink amide MBHA resin; loading: 0.5 mmol/g) (0.1 mmol) was placed into a vessel of appropriate size on the instrument, washed 6 times with NMP and deprotected using two treatments with 22% piperidine/NMP (2 and 8 min. each). One or two additional monitored deprotection steps were performed until the conditions of the monitoring option were satisfied (<10% difference between the last two conductivity-based deprotection peaks). The total deprotection time was 10-12 min. The first Fmoc-protected amino acid was coupled next using the following method: Fmoc-AA-OH (1 mmol, 10 eq.) was dissolved in 2 mL of NMP and activated by subsequent addition of 0.45 M HBTU/HOBt in DMF (2.2 mL) and 2 M DIEA/NMP (1 mL). The solution of the activated Fmoc-protected amino acid was then transferred to the reaction vessel and the coupling was allowed to proceed for 30 to 60 min., depending on the feedback from the deprotection steps. The resin was then washed 6 times with NMP, and subjected to the additional deprotection/coupling cycles as described above necessary to complete the assembly of the desired sequence. Finally, the Fmoc group was removed with 22% piperidine in NMP as described above, and the peptidyl-resin was washed 6 times with NMP and DCM, and dried in vacuo.

Cleavage/Deprotection

The desired peptide was cleaved/deprotected from its respective peptidyl-resin by treatment with a solution of TFA/water/tri-isopropylsilane (94:3:3) (5.0 mL/g of peptidyl-resin) for 2 hrs. The resin was filtered off, rinsed with TFA cleavage solution (2 mL), and the combined TFA filtrates were dried in vacuo. The resulting solid was triturated and washed with diethyl ether, and finally dried, to yield the crude peptide product as a white solid. This was purified by preparative HPLC as described herein. The fraction containing a pure product was lyophilized, to yield the pure peptide product in 20-40% isolated yield.

Example 20

Coupling of the Alexa488 Label to a EBP Peptide

The Alexa488 label was attached to either the α-amino group of the N-terminal amino acid residue of a EBP peptide or the ω-amino group of the side chain of a α,ω-diamino acid appended to the C-terminus of a EBP peptide by reaction of the purified EBP peptide with the N-hydroxysuccinimidyl ester of the Alexa Fluor® 488 fluorophore [1.5-2.0 eq.] for 16-20 hrs in NMP and DIEA (1-2 eq). The reaction progress was monitored by HPLC. The resulting Alexa488-labeled EBP peptide was then purified by HPLC and characterized as described herein.

Example 21

Biased Library Peptides Identified by Solution Panning at pH 5.2

Panning was performed at pH 5.2 to identify peptides that bind to the exosite under these conditions more tightly than was the case for the peptides derived from the unbiased libraries. The methods employed are identical to those described in Example 2, with the exception that Protein A cells were replaced by Protein A agarose beads (Sigma, St. Louis, Mo.) and that amounts of BACE, number of washes and temperatures of wash buffers were used as outlined below to maximize recovery of the tightest binding phage. More particularly, two biased M13-based peptide libraries were panned against BACE-Ig prepared from CHO cells, described herein above. Protein A beads were preblocked in 50 mM NaOAc, pH 5.2, +2% BSA for 2 hours. In parallel, BACE was incubated for two hours with library phage using the same buffer. Both samples were then mixed together for two hours. This step was followed by several washes and phage were eluted with 6M urea, pH 3.0, and used for amplification and further panning cycles or DNA sequencing after round three. Cycle 1:10 micrograms of BACE were used and 6 quick washes were carried out with PBS plus 0.2% Tween 20 at room temperature. Cycle 2: 50 nanograms of BACE were used and there were 7 washes of 3 minutes duration each with 50 mM NaOAc, pH 5.2, +0.2% Tween 20 at 37° C. Cycle 3: 25 nanograms of BACE were used and there were 15 washes of three minutes duration each using 0.3M NaOAc, pH 5.2, at 37° C.

Biased peptide libraries were employed in this Example. The biased libraries were made as described herein (see also, Sidhu et al., (2000) *Method Enzymol.* 328:333-363), except that the residues defining the core motif (i.e., HYPYFI (SEQ ID NO:54) were fixed in order to bias the peptides. Each X corresponds to one random library residue. All peptides in the table below are preferably synthesized with an added unblocked N-terminal Ala, while C-termini are preferably blocked. The libraries were designed as follows:

```
linear          XXXXXHYPYFIXXXXX    (SEQ ID NO:55)
library 1:

cyclic          CysXXXXXHYPYFIXXXXXCys  (SEQ ID NO:56)
library 2:
```

Peptides observed to bind to the BACE exosite at pH 5.2 are shown in the table presented below. In the table, the fixed motif is indicated by italics. Peptides are grouped into sets with shared sequence similarity within the random segments and those similarities are in bold. Potential disulfide bonds are indicated by underlining. 6 peptides gave the most improved phage ELISA binding signal relative to BMS-561871 on phage and are identified in the table by "XXX". The peptides marked XXX are all cyclic, one of which has a third internal Cys. Although it is not the inventors' desire to be bound to any theory of operation, it is noted that the peptide with the internal Cys may be interesting in a scenario in which the peptides bind through the fixed core motif and then sterically interfere with the access of substrate to the active site. In this case, it may be that this peptide, and others like it, are better inhibitors compared to other peptides that exhibit the same affinity.

TABLE 4

Exosite Binding Peptides Identified by Solution Panning at pH 5.2

| Sequence | SEQ ID | |
|---|---|---|
| TDQPK_HYPYFI_PSPHS | SEQ ID NO:58 | |
| THQPK_HYPYFI_PYHHD | SEQ ID NO:59 | |
| MDHEK_HYPYFI_EYKHV | SEQ ID NO:60 | |
| CTEANK_HYPYFI_PRHSSC | SEQ ID NO:61 | |
| HSLAP_HYPYFI_DLHST | SEQ ID NO:62 | |
| GSQAL_HYPYFI_PYHKH | SEQ ID NO:63 | |
| CTNKHD_HYPYFI_RPGEFC | SEQ ID NO:64 | |
| CENKHD_HYPYFI_SAGNYC | SEQ ID NO:65 | |
| CQTKVM_HYPYFI_REGVTC | SEQ ID NO:66 | |
| CGPKHL_HYPYFI_SATSRC | SEQ ID NO:67 | XXX |
| CAAKHS_HYPYFI_PA<u>CSSC</u> | SEQ ID NO:68 | |
| CASTYP_HYPYFI_AT<u>CKTC</u> | SEQ ID NO:69 | |
| CAEAKQ_HYPYFI_KW<u>CKTC</u> | SEQ ID NO:70 | |
| CAEAKG_HYPYFI_<u>CTTGNC</u> | SEQ ID NO:71 | |

TABLE 4-continued

Exosite Binding Peptides Identified by Solution Panning at pH 5.2

| Sequence | SEQ ID | |
|---|---|---|
| CAQARE_HYPYFI_DLRTV | SEQ ID NO:72 | |
| CAKAPR_HYPYFI_SAQNAW | SEQ ID NO:73 | |
| CAKASH_HYPYFI_NLANNG | SEQ ID NO:74 | |
| CARAIT_HYPYFI_PY<u>CEEC</u> | SEQ ID NO:75 | XXX |
| AVSQT_HYPYFI_PLSQA | SEQ ID NO:76 | |
| CEDRPT_HYPYFI_SLNKQC | SEQ ID NO:77 | |
| CKTQDN_HYPYFI_SLKKAC | SEQ ID NO:78 | |
| CQTKHQ_HYPYFI_SLTDAC | SEQ ID NO:79 | XXX |
| CTKAHT_HYPYFI_SNSKIC | SEQ ID NO:80 | |
| CHHKHT_HYPYFI_PNTKSC | SEQ ID NO:81 | |
| CSQHHT_HYPYFI_PSNGMC | SEQ ID NO:82 | XXX |
| CAVEAR_HYPYFI_NT<u>CSNC</u> | SEQ ID NO:83 | |
| <u>CS</u>VVNR_HYPYFI_NNS<u>SKC</u> | SEQ ID NO:84 | |
| <u>CTGC</u>AR_HYPYFI_EVSTQW | SEQ ID NO:85 | |
| CSNASH_HYPYFI_STHSTC | SEQ ID NO:86 | |
| CSNPTG_HYPYFI_SPQGTC | SEQ ID NO:87 | |
| CNSTPR_HYPYFI_SVNSTC | SEQ ID NO:88 | |
| CGVQLV_HYPYFL_PANSTC | SEQ ID NO:89 | |
| CARTPS_HYPYFI_SLPDRG | SEQ ID NO:90 | |
| CSAGHN_HYPYFI_TLPGYG | SEQ ID NO:91 | |
| CASQDY_HYPYFI_PSPAWG | SEQ ID NO:92 | |
| ELPFQ_HYPYFI_DLPPV | SEQ ID NO:93 | |
| MHPNP_HYPYFI_PLPTR | SEQ ID NO:94 | |
| <u>CDSC</u>VT_HYPYFI_NTPYKY | SEQ ID NO:95 | |
| CAKPKQ_HYPYFI_<u>CYPHEC</u> | SEQ ID NO:96 | |
| INKTQ_HYPYFI_EYPFH | SEQ ID NO:97 | |
| CPNTQH_HYPYFI_KVGEHC | SEQ ID NO:98 | XXX |
| CPDIAH_HYPYFI_DSKSHC | SEQ ID NO:99 | |
| CQPTRH_HYPYFI_DVTGRC | SEQ ID NO:100 | |
| CQNNHH_HYPYFI_TPTHVC | SEQ ID NO:101 | |
| CTTTHE_HYPYFI_DPREAC | SEQ ID NO:102 | XXX |
| CTTPSR_HYPYFI_DQLGHC | SEQ ID NO:103 | |
| CNANHT_HYPYFI_DISRKC | SEQ ID NO:104 | |

TABLE 4-continued

Exosite Binding Peptides Identified by
Solution Panning at pH 5.2

| | |
|---|---|
| QFTHK*HYPYFI*NISPG | SEQ ID NO:105 |
| CNMPHS*HYPYFI*NPHQSC | SEQ ID NO:106 |

Example 22

BACE Exosite Binding Studies of Peptide
BMS-655507 BACE Protein Preparation

BACE samples were prepared for isothermal titration calorimetry by extensive dialysis against freshly prepared buffer at 4° C. using 12,000-14,000 kDa MWCO dialysis membrane (UltraPURE, GIBCO BRL). The buffers used for these experiments were either Dulbecco's PBS (2 mM $KH_2PO_4$, 8 mM $Na_2HPO_4$, 137 mM NaCl, 3 mM KCl), pH 7.0, or 50 mM NaOAc, pH 4.5. The pH values were determined at room temperature. Following two changes of buffer (500 mL each), the protein (typically 2-3 mL) was removed from the membrane and centrifuged (5 min×4000 g, 4° C.) to remove particulates. Following dialysis, the dialysate was filtered (0.22 µm) and retained for preparation of the peptide samples (below) and rinsing the sample cell of the calorimeter between experiments. The protein was stored at 4° C. until needed for the calorimetry experiments. The protein concentration was determined by 10-fold dilution into the same buffer, and measuring the UV absorbance at 280 nm in a 1.00 cm pathlength cell (calculated value=1.22 au=1.00 mg/mL protein, based on mean glycosylated molecular weight=53.5 kDa, and given amino acid composition). Final concentrations used in isothermal titration calorimetry were typically 4-5 µM, containing a final concentration of 1% v/v DMSO.

Preparation of Peptide BMS-655507

The peptide BMS-655507 (Ac-His-Trp-Pro-Phe-Phe-Ile-Arg-Ser; SEQ ID NO:57) was dissolved in the buffer dialysate, and a volume of DMSO added to yield 1.0% v/v. The pH of the peptide solutions were adjusted as necessary to equal that of the buffer dialysate and protein sample (within 0.01 pH units). The concentrations of peptide were determined measuring the UV absorbance at 280 nm, using the molar extinction coefficient value of $\epsilon$=5630 $M^{-1}cm^{-1}$.

Isothermal Titration Calorimetry

Isothermal titration calorimetry experiments were performed with a VP-ITC instrument from MicroCal Inc. (Northampton, Mass.). The instrument was controlled with a personal computer, and thermally regulated at the desired experimental temperature (25° C.). Samples of BACE and peptides were degassed for 15 min at room temperature using a degassing unit (MicroCal) before loading into the sample chamber or syringe, respectively. Deionized, degassed water was loaded into the instrument reference chamber and used for all experiments. For each titration experiment, a fresh sample of BACE (typically 5 µM, 2.0 mL) was loaded into the instrument sample chamber (volume=1.438 mL), using a glass syringe, following the manufacturer's directions. Similarly, fresh peptide samples (typically 130-180 µM for BMS-655507, 0.3 mL total volume) were loaded into the instrument injecting syringe unit before each experiment.

Instrument Parameters

The temperature was maintained at 25° C. during the titration experiments. A power setting of 6.0 µCal/sec was used, and a syringe stirring rate of 300 rpm was used. The initial injection was kept at 1.5-2.0 µL and the data from this injection was not included in the analysis as a standard practice. To completely define the binding isotherm, typically a 3-fold to 4-fold excess of peptide was added during the course of the titration experiment, using ~8 injections per molar equivalent, or 4-7 µL (BMS-655507) per injection. The data collection time per injection was fixed at 360 sec, with a signal averaging time of 2 sec. The data was analyzed using the manufacturer's software (i.e. Origin 5.0 for ITC). Before molar heat calculations were done, background corrections were made on all peaks by subtracting the mean of the final 8-12 injections from all injections.

The calculated molar heat values were fitted to a single binding site model using the manufacturer's software to determine the binding stoichiometry (n), the association constant ($K_A$), the enthalpy of the reaction ($\Delta H$), and the entropy of the reaction ($\Delta S$). These values were used to calculate the dissociation constant ($K_d$) which is the reciprocal of $K_A$, and the Gibbs free energy of the reaction ($\Delta G$), which is related to the $K_A$, $\Delta H$, and $\Delta S$ by the following equations: $\Delta G = -RT (\ln(K_A)) = \Delta H - T\Delta S$ (Levine, *Physical Chemistry*, ($2^{nd}$ ed.), McGraw-Hill Co. (1983), p. 125).

The sample cell was cleaned between injections by washing extensively with filtered PBS or NaOAc buffer, $H_2O$, and again with filtered buffer. After multiple experiments, the sample cell and syringe were more extensively cleaned using manufacturer's recommendations with a detergent solution heated to 50° C., followed by extensive washing with $H_2O$, methanol, $H_2O$, and finally filtered buffer. Blank injections of buffer into buffer were then performed to establish sufficient cleaning and reproducible background before carrying out additional BACE-peptide experiments.

Results

Figure 14:
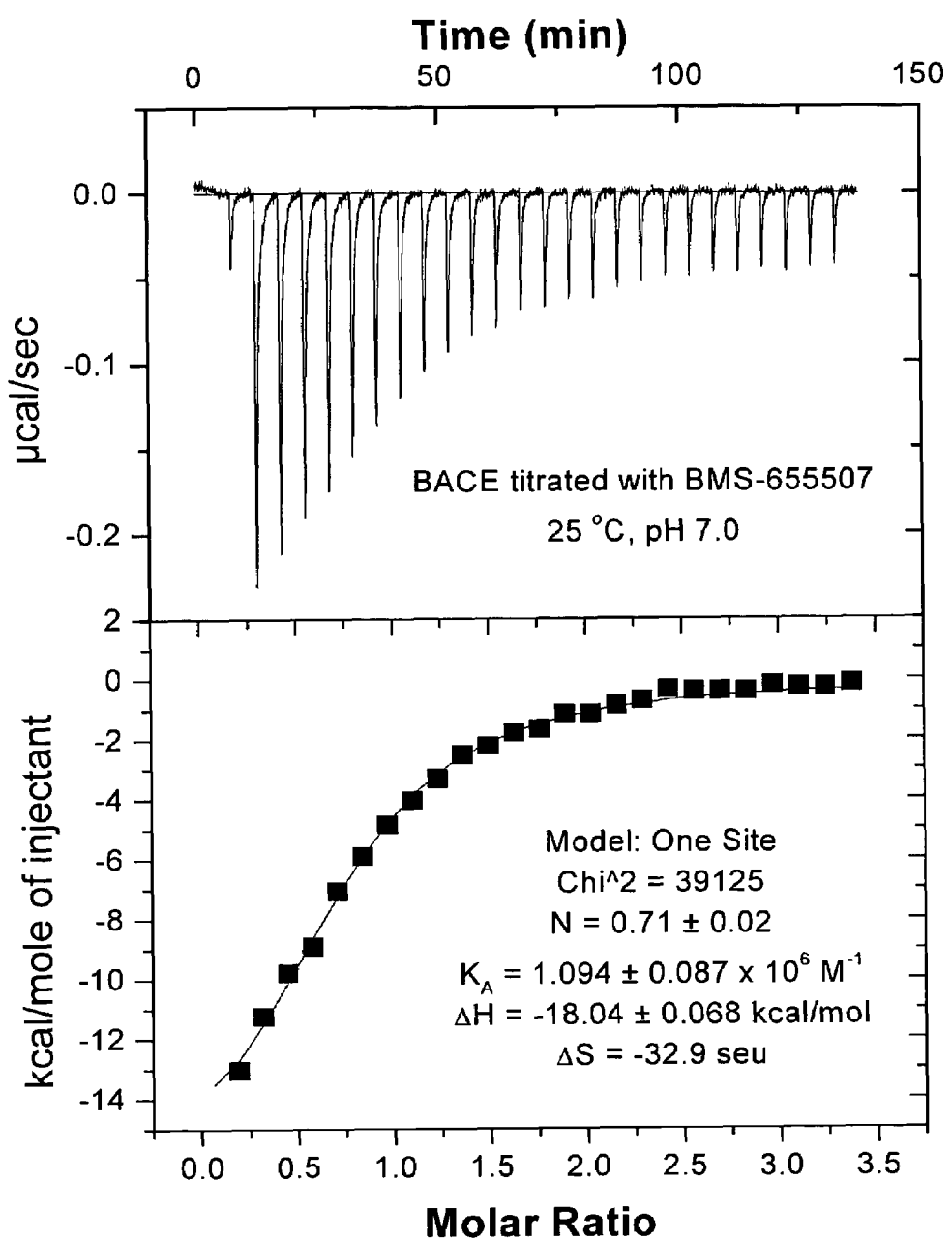
FIG. 14 shows integrated and fitted binding data for BACE and BMS-655507 (Ac-His-Trp-Pro-Phe-Phe-Ile-Arg-Ser; SEQ ID NO:57), at 25° C., in Dulbecco's PBS; parameters: $K_A=1.09\times10^6$ $M^{-1}$; $K_d=0.914$ μM; n=0.71; ΔH=−18.04 kcal/mol.
Figure 15:
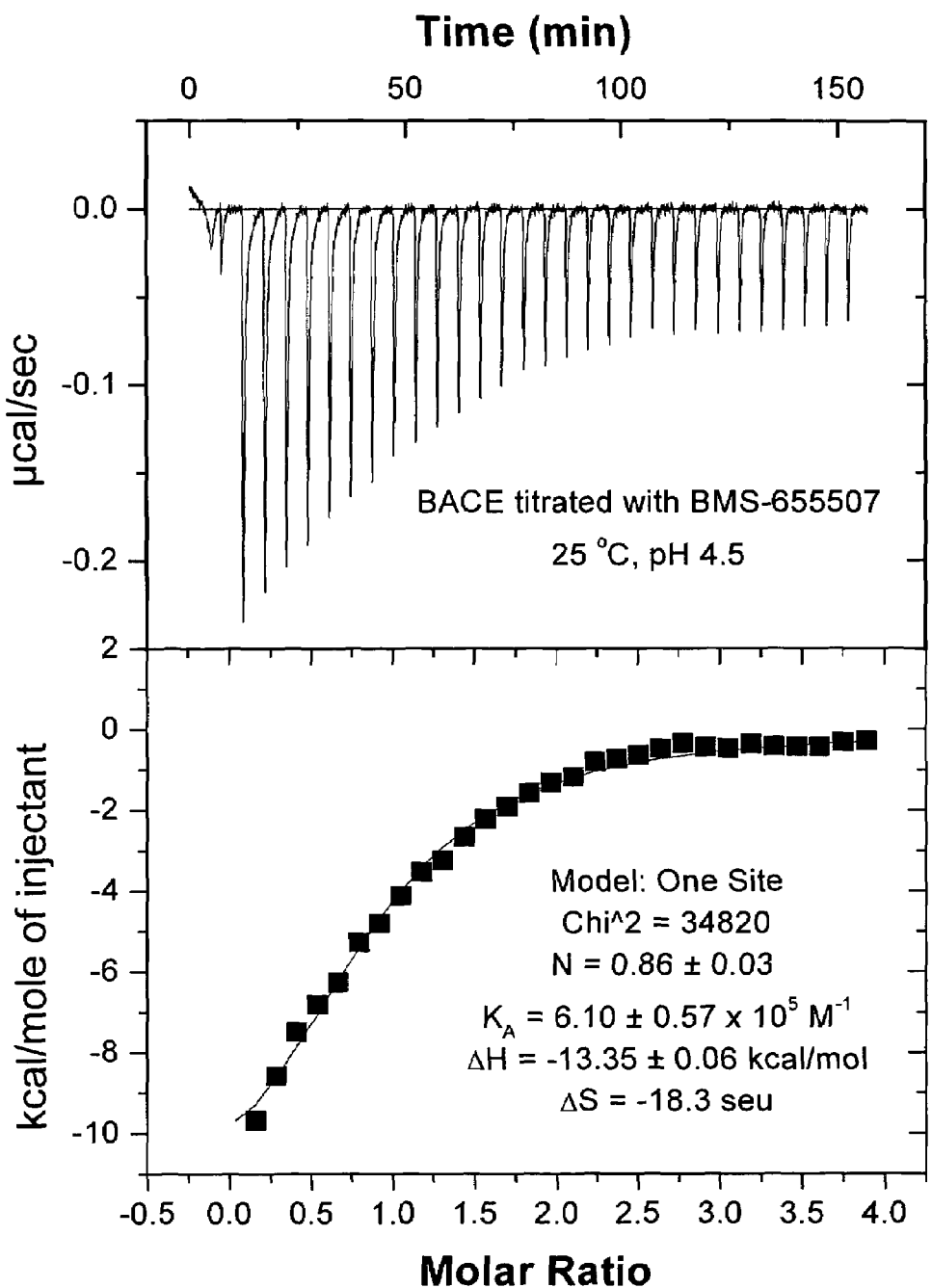
FIG. 15 shows integrated and fitted binding data for BACE and BMS-655507 (Ac-His-Trp-Pro-Phe-Phe-Ile-Arg-Ser; SEQ ID NO:57), at 25° C., in 50 mM NaOAc, pH 4.5; parameters: $K_A=6.10\times10^5$ $M^{-1}$; $K_d=1.64$ μM; n=0.86; ΔH=−13.35 kcal/mol.

Similar to previous experiments with BMS-561871 and BMS-561877, titrations of BMS-655507 into a solution containing BACE demonstrated saturable 1:1 binding. Experiments were completed in both Dulbecco's PBS, pH 7.0 and 50 mM NaOAc, pH 4.5, at 25° C. (FIGS. 14 and 15). The binding constants were determined to be $K_d$=0.914 µM for at pH 7.0 and $K_d$=1.64 µM at pH pH 4.5, as summarized in the following table.

TABLE 5

Calculated and Fitted Thermodynamic Data for Experiments with
BACE and BMS-655507 Conducted at pH 4.5 And 7.0, 25° C.

| pH value | $\Delta G$ (kcal/mol) | $\Delta H$ (kcal/mol) | $T\Delta S$ (kcal/mol) | $K_d$ (µM) | Stoichiometry |
|---|---|---|---|---|---|
| pH 4.5 | −7.90 | −13.35 | −5.46 | 1.64 | 0.86 |
| pH 7.0 | −8.23 | −18.04 | −9.81 | 0.914 | 0.71 |

Various publications are cited herein that are hereby incorporated by reference in their entirety.

As will be apparent to those skilled in the art to which the invention pertains, the present invention may be embodied in forms other than those specifically disclosed above without departing from the scope and spirit of the invention.

What is claimed is:

1. A method of identifying a peptide that specifically binds to a site other than the active site of Beta-APP cleaving enzyme, i.e., a BACE exosite, comprising:
   (a) contacting BACE with at least one peptide, wherein the at least one peptide comprises a Tyr-Pro-Tyr-Phe (SEQ ID NO:1) motif; and
   (b) determining whether the peptide specifically binds to BACE at a site other than the active site of BACE.

2. The method of claim 1, wherein the at least one peptide comprises from 5 to 30 amino acids.

3. A method of identifying a candidate peptide that specifically binds to a BACE exosite comprising:
   (a) contacting BACE with the candidate peptide and a BACE exosite binding peptide, wherein said BACE exosite binding peptide comprises a Tyr-Pro-Tyr-Phe (SEQ ID NO:1) motif and binds to the BACE exosite; and
   (b) determining whether the candidate peptide competes with said BACE exosite binding peptide for binding to the BACE exosite.

* * * * *

SEQUENCE LISTING

<160> NUMBER OF SEQ ID NOS: 109

<210> SEQ ID NO 1
<211> LENGTH: 4
<212> TYPE: PRT
<213> ORGANISM: Artificial
<220> FEATURE:
<223> OTHER INFORMATION: Synthesized Peptide

<400> SEQUENCE: 1

Tyr Pro Tyr Phe
1

<210> SEQ ID NO 2
<211> LENGTH: 5
<212> TYPE: PRT
<213> ORGANISM: Artificial
<220> FEATURE:
<223> OTHER INFORMATION: Synthesized Peptide

<400> SEQUENCE: 2

Tyr Pro Tyr Phe Ile
1               5

<210> SEQ ID NO 3
<211> LENGTH: 5
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa can be any naturally occurring amino acid

<400> SEQUENCE: 3

Xaa Tyr Pro Tyr Phe
1               5

<210> SEQ ID NO 4
<211> LENGTH: 6
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 4

Xaa Tyr Pro Tyr Phe Xaa
1               5

<210> SEQ ID NO 5
<211> LENGTH: 7
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (1)..(1)
<223> OTHER INFORMATION: Xaa can be any naturally occurring amino acid

```
<220> FEATURE:
<221> NAME/KEY: misc_feature
<222> LOCATION: (6)..(7)
<223> OTHER INFORMATION: Xaa can be any naturally occurring amino acid

<400> SEQUENCE: 5

Xaa Tyr Pro Tyr Phe Xaa Xaa
1               5

<210> SEQ ID NO 6
<211> LENGTH: 5
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 6

Tyr Pro Tyr Phe Xaa
1               5

<210> SEQ ID NO 7
<211> LENGTH: 6
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (5)..(6)
<223> OTHER INFORMATION: Xaa can be any naturally occurring amino acid

<400> SEQUENCE: 7

Tyr Pro Tyr Phe Xaa Xaa
1               5

<210> SEQ ID NO 8
<211> LENGTH: 5
<212> TYPE: PRT
<213> ORGANISM: Artificial
<220> FEATURE:
<223> OTHER INFORMATION: Synthesized Peptide

<400> SEQUENCE: 8

His Tyr Pro Tyr Phe
1               5

<210> SEQ ID NO 9
<211> LENGTH: 6
<212> TYPE: PRT
<213> ORGANISM: Artificial
<220> FEATURE:
<223> OTHER INFORMATION: Synthesized Peptide

<400> SEQUENCE: 9

Tyr Pro Tyr Phe Ile Pro
1               5

<210> SEQ ID NO 10
<211> LENGTH: 7
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
```

```
<222> LOCATION: (1)..(1)
<223> OTHER INFORMATION: wherein amino acid 1 may be acetylated
<220> FEATURE:
<221> NAME/KEY: MOD_RES
<222> LOCATION: (7)..(7)
<223> OTHER INFORMATION: wherein amino acid 7 may end with an amine

<400> SEQUENCE: 10

Tyr Pro Tyr Phe Ile Pro Leu
1               5

<210> SEQ ID NO 11
<211> LENGTH: 7
<212> TYPE: PRT
<213> ORGANISM: Artificial
<220> FEATURE:
<223> OTHER INFORMATION: Synthesized Peptide

<400> SEQUENCE: 11

Tyr Pro Tyr Phe Leu Pro Ile
1               5

<210> SEQ ID NO 12
<211> LENGTH: 7
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 12

Tyr Pro Tyr Phe Xaa Pro Ile
1               5

<210> SEQ ID NO 13
<211> LENGTH: 7
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 13

Tyr Pro Tyr Phe Xaa Pro Xaa
1               5

<210> SEQ ID NO 14
<211> LENGTH: 7
<212> TYPE: PRT
<213> ORGANISM: Artificial
<220> FEATURE:
<223> OTHER INFORMATION: Synthesized Peptide

<400> SEQUENCE: 14

His Tyr Pro Tyr Phe Ile Pro
1               5

<210> SEQ ID NO 15
<211> LENGTH: 5
```

```
<212> TYPE: PRT
<213> ORGANISM: Artificial
<220> FEATURE:
<223> OTHER INFORMATION: Synthesized Peptide

<400> SEQUENCE: 15

Tyr Pro Tyr Phe Leu
1               5

<210> SEQ ID NO 16
<211> LENGTH: 6
<212> TYPE: PRT
<213> ORGANISM: Artificial
<220> FEATURE:
<223> OTHER INFORMATION: Synthesized Peptide

<400> SEQUENCE: 16

Tyr Pro Tyr Phe Leu Pro
1               5

<210> SEQ ID NO 17
<211> LENGTH: 7
<212> TYPE: PRT
<213> ORGANISM: Artificial
<220> FEATURE:
<223> OTHER INFORMATION: Synthesized Peptide

<400> SEQUENCE: 17

His Tyr Pro Tyr Phe Leu Pro
1               5

<210> SEQ ID NO 18
<211> LENGTH: 8
<212> TYPE: PRT
<213> ORGANISM: Artificial
<220> FEATURE:
<223> OTHER INFORMATION: Synthesized Peptide

<400> SEQUENCE: 18

His Tyr Pro Tyr Phe Ile Pro Leu
1               5

<210> SEQ ID NO 19
<211> LENGTH: 12
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (12)..(12)
<223> OTHER INFORMATION: wherein amino acid ends with an amine

<400> SEQUENCE: 19

Asn Leu Thr Thr Tyr Pro Tyr Phe Ile Pro Leu Pro
1               5                   10

<210> SEQ ID NO 20
<211> LENGTH: 12
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (12)..(12)
<223> OTHER INFORMATION: wherein the amino acid ends with an amine

<400> SEQUENCE: 20
```

```
Ala Leu Tyr Pro Tyr Phe Leu Pro Ile Ser Ala Lys
1               5                   10
```

<210> SEQ ID NO 21
<211> LENGTH: 5
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<223> OTHER INFORMATION: wherein Xaa is any amino acid
<220> FEATURE:
<221> NAME/KEY: misc_feature
<222> LOCATION: (3)..(3)
<223> OTHER INFORMATION: Xaa can be any naturally occurring amino acid

<400> SEQUENCE: 21

```
Trp Pro Xaa Phe Ile
1               5
```

<210> SEQ ID NO 22
<211> LENGTH: 23
<212> TYPE: PRT
<213> ORGANISM: Artificial
<220> FEATURE:
<223> OTHER INFORMATION: Synthesized Peptide

<400> SEQUENCE: 22

```
Glu Thr Trp Pro Arg Phe Ile Pro Tyr His Ala Leu Thr Gln Gln Thr
1               5                   10                  15

Leu Lys His Gln Gln His Thr
            20
```

<210> SEQ ID NO 23
<211> LENGTH: 27
<212> TYPE: PRT
<213> ORGANISM: Artificial
<220> FEATURE:
<223> OTHER INFORMATION: Synthesized Peptide

<400> SEQUENCE: 23

```
Thr Ala Glu Tyr Glu Ser Arg Thr Ala Arg Thr Ala Pro Pro Ala Pro
1               5                   10                  15

Thr Gln His Trp Pro Phe Phe Ile Arg Ser Thr
            20                  25
```

<210> SEQ ID NO 24
<211> LENGTH: 12
<212> TYPE: PRT
<213> ORGANISM: Artificial
<220> FEATURE:
<223> OTHER INFORMATION: Synthesized Peptide

<400> SEQUENCE: 24

```
Gln Asn His Tyr Pro Tyr Phe Ile Ala Val Pro Ile
1               5                   10
```

<210> SEQ ID NO 25
<211> LENGTH: 12
<212> TYPE: PRT
<213> ORGANISM: Artificial
<220> FEATURE:
<223> OTHER INFORMATION: Synthesized Peptide

<400> SEQUENCE: 25

```
Glu Gly Asn Lys His Tyr Pro Tyr Phe Ile Lys Val
1               5                   10
```

<210> SEQ ID NO 26
<211> LENGTH: 12
<212> TYPE: PRT
<213> ORGANISM: Artificial
<220> FEATURE:
<223> OTHER INFORMATION: Synthesized Peptide

<400> SEQUENCE: 26

```
Thr His Ser His Tyr Pro Tyr Phe Ile Glu Leu Glu
1               5                   10
```

<210> SEQ ID NO 27
<211> LENGTH: 12
<212> TYPE: PRT
<213> ORGANISM: Artificial
<220> FEATURE:
<223> OTHER INFORMATION: Synthesized Peptide

<400> SEQUENCE: 27

```
Gln Gln Tyr Pro Tyr Phe Ile Pro Val Ile Arg Pro
1               5                   10
```

<210> SEQ ID NO 28
<211> LENGTH: 12
<212> TYPE: PRT
<213> ORGANISM: Artificial
<220> FEATURE:
<223> OTHER INFORMATION: Synthesized Peptide

<400> SEQUENCE: 28

```
His Tyr Pro Tyr Phe Leu Pro Leu His Thr Pro Lys
1               5                   10
```

<210> SEQ ID NO 29
<211> LENGTH: 24
<212> TYPE: PRT
<213> ORGANISM: Artificial
<220> FEATURE:
<223> OTHER INFORMATION: Synthesized Peptide

<400> SEQUENCE: 29

```
Ala Met Leu Asp Gly Ala Pro Thr Asn Arg Asn Ser Gln His Tyr Pro
1               5                   10                  15

Tyr Phe Leu Pro Ile Ala Thr Val
            20
```

<210> SEQ ID NO 30
<211> LENGTH: 23
<212> TYPE: PRT
<213> ORGANISM: Artificial
<220> FEATURE:
<223> OTHER INFORMATION: Synthesized Peptide

<400> SEQUENCE: 30

```
Leu Pro Val Tyr Asp Thr Thr Ala Pro Thr His Tyr Pro Tyr Phe Leu
1               5                   10                  15

Pro Leu Pro Arg Ile Ser Pro
            20
```

<210> SEQ ID NO 31
<211> LENGTH: 12
<212> TYPE: PRT
<213> ORGANISM: Artificial

```
<220> FEATURE:
<223> OTHER INFORMATION: Synthesized Peptide

<400> SEQUENCE: 31

Ser Gln Leu Gln His Tyr Pro Tyr Phe Arg Pro Leu
1               5                   10

<210> SEQ ID NO 32
<211> LENGTH: 12
<212> TYPE: PRT
<213> ORGANISM: Artificial
<220> FEATURE:
<223> OTHER INFORMATION: Synthesized Peptide

<400> SEQUENCE: 32

Tyr Ile Pro His Tyr Pro Tyr Phe Ile Arg Leu Asn
1               5                   10

<210> SEQ ID NO 33
<211> LENGTH: 23
<212> TYPE: PRT
<213> ORGANISM: Artificial
<220> FEATURE:
<223> OTHER INFORMATION: Synthesized Peptide

<400> SEQUENCE: 33

Lys Met His Ser Met Ile Asn Gln Leu Gly Thr Arg His Tyr Pro Tyr
1               5                   10                  15

Phe Arg Glu Ile Asn Asp Tyr
            20

<210> SEQ ID NO 34
<211> LENGTH: 12
<212> TYPE: PRT
<213> ORGANISM: Artificial
<220> FEATURE:
<223> OTHER INFORMATION: Synthesized Peptide

<400> SEQUENCE: 34

Gly Ser Thr Lys Ser Tyr Pro Tyr Phe Ile His Thr
1               5                   10

<210> SEQ ID NO 35
<211> LENGTH: 23
<212> TYPE: PRT
<213> ORGANISM: Artificial
<220> FEATURE:
<223> OTHER INFORMATION: Synthesized Peptide

<400> SEQUENCE: 35

Asp Ile Trp Asn Gly Ala Lys Ala Pro Lys Asn Ser Met Tyr Pro Tyr
1               5                   10                  15

Phe Ile Pro Ser Ser Leu Lys
            20

<210> SEQ ID NO 36
<211> LENGTH: 27
<212> TYPE: PRT
<213> ORGANISM: Artificial
<220> FEATURE:
<223> OTHER INFORMATION: Synthesized Peptide

<400> SEQUENCE: 36

Ile Ser Val Ile Asn Gln Pro Ala Gln Asn Met His Pro Arg Gln Met
1               5                   10                  15
```

Thr Ala Tyr Pro Tyr Phe Arg Pro Ile Ser Arg
            20                  25

<210> SEQ ID NO 37
<211> LENGTH: 23
<212> TYPE: PRT
<213> ORGANISM: Artificial
<220> FEATURE:
<223> OTHER INFORMATION: Synthesized Peptide

<400> SEQUENCE: 37

Asp Val Tyr Pro Tyr Phe Val Ser Ser Asn Glu Gly His Ser Ile Arg
1               5                   10                  15

His Lys Gly Asn Asn Ser Leu
            20

<210> SEQ ID NO 38
<211> LENGTH: 33
<212> TYPE: PRT
<213> ORGANISM: Artificial
<220> FEATURE:
<223> OTHER INFORMATION: Synthesized Peptide

<400> SEQUENCE: 38

Tyr Pro Tyr Phe Ile Asp Ser His Pro Pro Lys Glu Leu Met Pro His
1               5                   10                  15

Ser Trp Val Gln Ser Lys Tyr Pro Ala Ser Pro Gln Thr His Thr Thr
            20                  25                  30

Tyr

<210> SEQ ID NO 39
<211> LENGTH: 12
<212> TYPE: PRT
<213> ORGANISM: Artificial
<220> FEATURE:
<223> OTHER INFORMATION: Synthesized Peptide

<400> SEQUENCE: 39

Gly Tyr Pro Tyr Phe Leu Asn Leu Lys Asn Ser His
1               5                   10

<210> SEQ ID NO 40
<211> LENGTH: 12
<212> TYPE: PRT
<213> ORGANISM: Artificial
<220> FEATURE:
<223> OTHER INFORMATION: Synthesized Peptide

<400> SEQUENCE: 40

Asn Ser Tyr Pro Tyr Phe Ile His Leu Ser Asn Pro
1               5                   10

<210> SEQ ID NO 41
<211> LENGTH: 12
<212> TYPE: PRT
<213> ORGANISM: Artificial
<220> FEATURE:
<223> OTHER INFORMATION: Synthesized Peptide

<400> SEQUENCE: 41

His Asp Tyr Pro Tyr Phe Met Met Leu Thr Gly His
1               5                   10

<210> SEQ ID NO 42
<211> LENGTH: 12

```
<212> TYPE: PRT
<213> ORGANISM: Artificial
<220> FEATURE:
<223> OTHER INFORMATION: Synthesized Peptide

<400> SEQUENCE: 42

Gln Ile Glu Thr Tyr Pro Tyr Phe Leu Pro Ile Leu
 1               5                  10

<210> SEQ ID NO 43
<211> LENGTH: 12
<212> TYPE: PRT
<213> ORGANISM: Artificial
<220> FEATURE:
<223> OTHER INFORMATION: Synthesized Peptide

<400> SEQUENCE: 43

Tyr Tyr Pro Tyr Phe Ile Ser Thr Ala Arg Glu Val
 1               5                  10

<210> SEQ ID NO 44
<211> LENGTH: 11
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (11)..(11)
<223> OTHER INFORMATION: wherein amino acid 11 may end with an amine

<400> SEQUENCE: 44

Leu Thr Thr Tyr Pro Tyr Phe Ile Pro Leu Pro
 1               5                  10

<210> SEQ ID NO 45
<211> LENGTH: 10
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (10)..(10)
<223> OTHER INFORMATION: wherein amino acid 10 may end with an amine

<400> SEQUENCE: 45

Thr Thr Tyr Pro Tyr Phe Ile Pro Leu Pro
 1               5                  10

<210> SEQ ID NO 46
<211> LENGTH: 9
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (9)..(9)
```

<223> OTHER INFORMATION: wherein amino acid 9 may end with an amine

<400> SEQUENCE: 46

Thr Tyr Pro Tyr Phe Ile Pro Leu Pro
1               5

<210> SEQ ID NO 47
<211> LENGTH: 8
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (8)..(8)
<223> OTHER INFORMATION: wherein amino acid 8 may end with an amine

<400> SEQUENCE: 47

Tyr Pro Tyr Phe Ile Pro Leu Pro
1               5

<210> SEQ ID NO 48
<211> LENGTH: 11
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (11)..(11)
<223> OTHER INFORMATION: wherein amino acid 11 may end with an amine

<400> SEQUENCE: 48

Asn Leu Thr Thr Tyr Pro Tyr Phe Ile Pro Leu
1               5                   10

<210> SEQ ID NO 49
<211> LENGTH: 7
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: wherein amino acid 7 may end with an amine

<400> SEQUENCE: 49

Tyr Pro Tyr Phe Ile Ala Leu
1               5

<210> SEQ ID NO 50
<211> LENGTH: 7
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: wherein amino acid 1 may be acylated
<220> FEATURE:
<221> NAME/KEY: MOD_RES

```
<222> LOCATION: (7)..(7)
<223> OTHER INFORMATION: wherein amino acid 7 may end with an amine

<400> SEQUENCE: 50

Tyr Pro Tyr Phe Ile Pro Ala
1               5

<210> SEQ ID NO 51
<211> LENGTH: 6
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: wherein amino acid 1 may be acylated
<220> FEATURE:
<221> NAME/KEY: MOD_RES
<222> LOCATION: (2)..(3)
<223> OTHER INFORMATION: wherein Pro2 may be joined to Phe3 by a
                        p-benzoyl phenylalanine

<400> SEQUENCE: 51

Tyr Pro Phe Ile Pro Leu
1               5

<210> SEQ ID NO 52
<211> LENGTH: 6
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (6)..(6)
<223> OTHER INFORMATION: wherein amino acid 6 may end with a p-benzoyl
                        phenalanine

<400> SEQUENCE: 52

Tyr Pro Tyr Phe Ile Pro
1               5

<210> SEQ ID NO 53
<211> LENGTH: 7
<212> TYPE: PRT
<213> ORGANISM: Artificial
<220> FEATURE:
<223> OTHER INFORMATION: Synthesized Peptide

<400> SEQUENCE: 53

Leu Tyr Pro Pro Tyr Ile Phe
1               5

<210> SEQ ID NO 54
<211> LENGTH: 6
<212> TYPE: PRT
<213> ORGANISM: Artificial
<220> FEATURE:
<223> OTHER INFORMATION: motif

<400> SEQUENCE: 54

His Tyr Pro Tyr Phe Ile
1               5
```

```
<210> SEQ ID NO 55
<211> LENGTH: 16
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (1)..(5)
<223> OTHER INFORMATION: Xaa can be any naturally occurring amino acid
<220> FEATURE:
<221> NAME/KEY: misc_feature
<222> LOCATION: (12)..(16)
<223> OTHER INFORMATION: Xaa can be any naturally occurring amino acid

<400> SEQUENCE: 55

Xaa Xaa Xaa Xaa Xaa His Tyr Pro Tyr Phe Ile Xaa Xaa Xaa Xaa Xaa
1               5                   10                  15

<210> SEQ ID NO 56
<211> LENGTH: 18
<212> TYPE: PRT
<213> ORGANISM: Artificial
<220> FEATURE:
<223> OTHER INFORMATION: Synthesized Peptide
<220> FEATURE:
<221> NAME/KEY: misc_feature
<222> LOCATION: (2)..(6)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid

<400> SEQUENCE: 56

Cys Xaa Xaa Xaa Xaa Xaa His Tyr Pro Tyr Phe Ile Xaa Xaa Xaa Xaa
1               5                   10                  15

Xaa Cys

<210> SEQ ID NO 57
<211> LENGTH: 8
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: wherein amino acid 1 may be acetylated
<220> FEATURE:
<221> NAME/KEY: MOD_RES
<222> LOCATION: (8)..(8)
<223> OTHER INFORMATION: wherein amino acid 8 may end with an amine

<400> SEQUENCE: 57

His Trp Pro Phe Phe Ile Arg Ser
1               5

<210> SEQ ID NO 58
<211> LENGTH: 16
<212> TYPE: PRT
<213> ORGANISM: Artificial
<220> FEATURE:
<223> OTHER INFORMATION: Synthesized Peptide

<400> SEQUENCE: 58

Thr Asp Gln Pro Lys His Tyr Pro Tyr Phe Ile Pro Ser Pro His Ser
1               5                   10                  15

<210> SEQ ID NO 59
```

```
<211> LENGTH: 16
<212> TYPE: PRT
<213> ORGANISM: Artificial
<220> FEATURE:
<223> OTHER INFORMATION: Synthesized Peptide

<400> SEQUENCE: 59

Thr His Gln Pro Lys His Tyr Pro Tyr Phe Ile Pro Tyr His His Asp
1               5                   10                  15

<210> SEQ ID NO 60
<211> LENGTH: 16
<212> TYPE: PRT
<213> ORGANISM: Artificial
<220> FEATURE:
<223> OTHER INFORMATION: Synthesized Peptide

<400> SEQUENCE: 60

Met Asp His Glu Lys His Tyr Pro Tyr Phe Ile Glu Tyr Lys His Val
1               5                   10                  15

<210> SEQ ID NO 61
<211> LENGTH: 18
<212> TYPE: PRT
<213> ORGANISM: Artificial
<220> FEATURE:
<223> OTHER INFORMATION: Synthesized Peptide

<400> SEQUENCE: 61

Cys Thr Glu Ala Asn Lys His Tyr Pro Tyr Phe Ile Pro Arg His Ser
1               5                   10                  15

Ser Cys

<210> SEQ ID NO 62
<211> LENGTH: 16
<212> TYPE: PRT
<213> ORGANISM: Artificial
<220> FEATURE:
<223> OTHER INFORMATION: Synthesized Peptide

<400> SEQUENCE: 62

His Ser Leu Ala Pro His Tyr Pro Tyr Phe Ile Asp Leu His Ser Thr
1               5                   10                  15

<210> SEQ ID NO 63
<211> LENGTH: 16
<212> TYPE: PRT
<213> ORGANISM: Artificial
<220> FEATURE:
<223> OTHER INFORMATION: Synthesized Peptide

<400> SEQUENCE: 63

Gly Ser Gln Ala Leu His Tyr Pro Tyr Phe Ile Pro Tyr His Lys His
1               5                   10                  15

<210> SEQ ID NO 64
<211> LENGTH: 18
<212> TYPE: PRT
<213> ORGANISM: Artificial
<220> FEATURE:
<223> OTHER INFORMATION: Synthesized Peptide

<400> SEQUENCE: 64

Cys Thr Asn Lys His Asp His Tyr Pro Tyr Phe Ile Arg Pro Gly Glu
1               5                   10                  15

Phe Cys
```

```
<210> SEQ ID NO 65
<211> LENGTH: 18
<212> TYPE: PRT
<213> ORGANISM: Artificial
<220> FEATURE:
<223> OTHER INFORMATION: Synthesized Peptide

<400> SEQUENCE: 65

Cys Glu Asn Lys His Asp His Tyr Pro Tyr Phe Ile Ser Ala Gly Asn
1               5                   10                  15

Tyr Cys

<210> SEQ ID NO 66
<211> LENGTH: 18
<212> TYPE: PRT
<213> ORGANISM: Artificial
<220> FEATURE:
<223> OTHER INFORMATION: Synthesized Peptide

<400> SEQUENCE: 66

Cys Gln Thr Lys Val Met His Tyr Pro Tyr Phe Ile Arg Glu Gly Val
1               5                   10                  15

Thr Cys

<210> SEQ ID NO 67
<211> LENGTH: 18
<212> TYPE: PRT
<213> ORGANISM: Artificial
<220> FEATURE:
<223> OTHER INFORMATION: Synthesized Peptide

<400> SEQUENCE: 67

Cys Gly Pro Lys His Leu His Tyr Pro Tyr Phe Ile Ser Ala Thr Ser
1               5                   10                  15

Arg Cys

<210> SEQ ID NO 68
<211> LENGTH: 18
<212> TYPE: PRT
<213> ORGANISM: Artificial
<220> FEATURE:
<223> OTHER INFORMATION: Synthesized Peptide

<400> SEQUENCE: 68

Cys Ala Ala Lys His Ser His Tyr Pro Tyr Phe Ile Pro Ala Cys Ser
1               5                   10                  15

Ser Cys

<210> SEQ ID NO 69
<211> LENGTH: 18
<212> TYPE: PRT
<213> ORGANISM: Artificial
<220> FEATURE:
<223> OTHER INFORMATION: Synthesized Peptide

<400> SEQUENCE: 69

Cys Ala Ser Thr Tyr Pro His Tyr Pro Tyr Phe Ile Ala Thr Cys Lys
1               5                   10                  15

Thr Cys

<210> SEQ ID NO 70
<211> LENGTH: 18
```

<212> TYPE: PRT
<213> ORGANISM: Artificial
<220> FEATURE:
<223> OTHER INFORMATION: Synthesized Peptide

<400> SEQUENCE: 70

Cys Ala Glu Ala Lys Gln His Tyr Pro Tyr Phe Ile Lys Trp Cys Lys
1               5                   10                  15
Thr Cys

<210> SEQ ID NO 71
<211> LENGTH: 18
<212> TYPE: PRT
<213> ORGANISM: Artificial
<220> FEATURE:
<223> OTHER INFORMATION: Synthesized Peptide

<400> SEQUENCE: 71

Cys Ala Glu Ala Lys Gly His Tyr Pro Tyr Phe Ile Cys Thr Thr Gly
1               5                   10                  15
Asn Cys

<210> SEQ ID NO 72
<211> LENGTH: 17
<212> TYPE: PRT
<213> ORGANISM: Artificial
<220> FEATURE:
<223> OTHER INFORMATION: Synthesized Peptide

<400> SEQUENCE: 72

Cys Ala Gln Ala Arg Glu His Tyr Pro Tyr Phe Ile Asp Leu Arg Thr
1               5                   10                  15
Val

<210> SEQ ID NO 73
<211> LENGTH: 18
<212> TYPE: PRT
<213> ORGANISM: Artificial
<220> FEATURE:
<223> OTHER INFORMATION: Synthesized Peptide

<400> SEQUENCE: 73

Cys Ala Lys Ala Pro Arg His Tyr Pro Tyr Phe Ile Ser Ala Gln Asn
1               5                   10                  15
Ala Trp

<210> SEQ ID NO 74
<211> LENGTH: 18
<212> TYPE: PRT
<213> ORGANISM: Artificial
<220> FEATURE:
<223> OTHER INFORMATION: Synthesized Peptide

<400> SEQUENCE: 74

Cys Ala Lys Ala Ser His His Tyr Pro Tyr Phe Ile Asn Leu Ala Asn
1               5                   10                  15
Asn Gly

<210> SEQ ID NO 75
<211> LENGTH: 18
<212> TYPE: PRT
<213> ORGANISM: Artificial
<220> FEATURE:
<223> OTHER INFORMATION: Synthesized Peptide

```
<400> SEQUENCE: 75

Cys Ala Arg Ala Ile Thr His Tyr Pro Tyr Phe Ile Pro Tyr Cys Glu
1               5                   10                  15

Glu Cys

<210> SEQ ID NO 76
<211> LENGTH: 16
<212> TYPE: PRT
<213> ORGANISM: Artificial
<220> FEATURE:
<223> OTHER INFORMATION: Synthesized Peptide

<400> SEQUENCE: 76

Ala Val Ser Gln Thr His Tyr Pro Tyr Phe Ile Pro Leu Ser Gln Ala
1               5                   10                  15

<210> SEQ ID NO 77
<211> LENGTH: 18
<212> TYPE: PRT
<213> ORGANISM: Artificial
<220> FEATURE:
<223> OTHER INFORMATION: Synthesized Peptide

<400> SEQUENCE: 77

Cys Glu Asp Arg Pro Thr His Tyr Pro Tyr Phe Ile Ser Leu Asn Lys
1               5                   10                  15

Gln Cys

<210> SEQ ID NO 78
<211> LENGTH: 18
<212> TYPE: PRT
<213> ORGANISM: Artificial
<220> FEATURE:
<223> OTHER INFORMATION: Synthesized Peptide

<400> SEQUENCE: 78

Cys Lys Thr Gln Asp Asn His Tyr Pro Tyr Phe Ile Ser Leu Lys Lys
1               5                   10                  15

Ala Cys

<210> SEQ ID NO 79
<211> LENGTH: 18
<212> TYPE: PRT
<213> ORGANISM: Artificial
<220> FEATURE:
<223> OTHER INFORMATION: Synthesized Peptide

<400> SEQUENCE: 79

Cys Gln Thr Lys His Gln His Tyr Pro Tyr Phe Ile Ser Leu Thr Asp
1               5                   10                  15

Ala Cys

<210> SEQ ID NO 80
<211> LENGTH: 18
<212> TYPE: PRT
<213> ORGANISM: Artificial
<220> FEATURE:
<223> OTHER INFORMATION: Synthesized Peptide

<400> SEQUENCE: 80

Cys Thr Lys Ala His Thr His Tyr Pro Tyr Phe Ile Ser Asn Ser Lys
1               5                   10                  15
```

Ile Cys

<210> SEQ ID NO 81
<211> LENGTH: 18
<212> TYPE: PRT
<213> ORGANISM: Artificial
<220> FEATURE:
<223> OTHER INFORMATION: Synthesized Peptide

<400> SEQUENCE: 81

Cys His His Lys His Thr His Tyr Pro Tyr Phe Ile Pro Asn Thr Lys
1               5                   10                  15

Ser Cys

<210> SEQ ID NO 82
<211> LENGTH: 18
<212> TYPE: PRT
<213> ORGANISM: Artificial
<220> FEATURE:
<223> OTHER INFORMATION: Synthesized Peptide

<400> SEQUENCE: 82

Cys Ser Gln His His Thr His Tyr Pro Tyr Phe Ile Pro Ser Asn Gly
1               5                   10                  15

Met Cys

<210> SEQ ID NO 83
<211> LENGTH: 18
<212> TYPE: PRT
<213> ORGANISM: Artificial
<220> FEATURE:
<223> OTHER INFORMATION: Synthesized Peptide

<400> SEQUENCE: 83

Cys Ala Val Glu Ala Arg His Tyr Pro Tyr Phe Ile Asn Thr Cys Ser
1               5                   10                  15

Asn Cys

<210> SEQ ID NO 84
<211> LENGTH: 18
<212> TYPE: PRT
<213> ORGANISM: Artificial
<220> FEATURE:
<223> OTHER INFORMATION: Synthesized Peptide

<400> SEQUENCE: 84

Cys Ser Val Val Asn Arg His Tyr Pro Tyr Phe Ile Asn Asn Ser Ser
1               5                   10                  15

Lys Cys

<210> SEQ ID NO 85
<211> LENGTH: 18
<212> TYPE: PRT
<213> ORGANISM: Artificial
<220> FEATURE:
<223> OTHER INFORMATION: Synthesized Peptide

<400> SEQUENCE: 85

Cys Thr Gly Cys Ala Arg His Tyr Pro Tyr Phe Ile Glu Val Ser Thr
1               5                   10                  15

Gln Trp

<210> SEQ ID NO 86

<211> LENGTH: 18
<212> TYPE: PRT
<213> ORGANISM: Artificial
<220> FEATURE:
<223> OTHER INFORMATION: Synthesized Peptide

<400> SEQUENCE: 86

Cys Ser Asn Ala Ser His His Tyr Pro Tyr Phe Ile Ser Thr His Ser
1               5                   10                  15

Thr Cys

<210> SEQ ID NO 87
<211> LENGTH: 18
<212> TYPE: PRT
<213> ORGANISM: Artificial
<220> FEATURE:
<223> OTHER INFORMATION: Synthesized Peptide

<400> SEQUENCE: 87

Cys Ser Asn Pro Thr Gly His Tyr Pro Tyr Phe Ile Ser Pro Gln Gly
1               5                   10                  15

Thr Cys

<210> SEQ ID NO 88
<211> LENGTH: 18
<212> TYPE: PRT
<213> ORGANISM: Artificial
<220> FEATURE:
<223> OTHER INFORMATION: Synthesized Peptide

<400> SEQUENCE: 88

Cys Asn Ser Thr Pro Arg His Tyr Pro Tyr Phe Ile Ser Val Asn Ser
1               5                   10                  15

Thr Cys

<210> SEQ ID NO 89
<211> LENGTH: 18
<212> TYPE: PRT
<213> ORGANISM: Artificial
<220> FEATURE:
<223> OTHER INFORMATION: Synthesized Peptide

<400> SEQUENCE: 89

Cys Gly Val Gln Leu Val His Tyr Pro Tyr Phe Leu Pro Ala Asn Ser
1               5                   10                  15

Thr Cys

<210> SEQ ID NO 90
<211> LENGTH: 18
<212> TYPE: PRT
<213> ORGANISM: Artificial
<220> FEATURE:
<223> OTHER INFORMATION: Synthesized Peptide

<400> SEQUENCE: 90

Cys Ala Arg Thr Pro Ser His Tyr Pro Tyr Phe Ile Ser Leu Pro Asp
1               5                   10                  15

Arg Gly

<210> SEQ ID NO 91
<211> LENGTH: 18
<212> TYPE: PRT
<213> ORGANISM: Artificial
<220> FEATURE:

<223> OTHER INFORMATION: Synthesized Peptide

<400> SEQUENCE: 91

Cys Ser Ala Gly His Asn His Tyr Pro Tyr Phe Ile Thr Leu Pro Gly
1               5                   10                  15

Tyr Gly

<210> SEQ ID NO 92
<211> LENGTH: 18
<212> TYPE: PRT
<213> ORGANISM: Artificial
<220> FEATURE:
<223> OTHER INFORMATION: Synthesized Peptide

<400> SEQUENCE: 92

Cys Ala Ser Gln Asp Tyr His Tyr Pro Tyr Phe Ile Pro Ser Pro Ala
1               5                   10                  15

Trp Gly

<210> SEQ ID NO 93
<211> LENGTH: 16
<212> TYPE: PRT
<213> ORGANISM: Artificial
<220> FEATURE:
<223> OTHER INFORMATION: Synthesized Peptide

<400> SEQUENCE: 93

Glu Leu Pro Phe Gln His Tyr Pro Tyr Phe Ile Asp Leu Pro Pro Val
1               5                   10                  15

<210> SEQ ID NO 94
<211> LENGTH: 16
<212> TYPE: PRT
<213> ORGANISM: Artificial
<220> FEATURE:
<223> OTHER INFORMATION: Synthesized Peptide

<400> SEQUENCE: 94

Met His Pro Asn Pro His Tyr Pro Tyr Phe Ile Pro Leu Pro Thr Arg
1               5                   10                  15

<210> SEQ ID NO 95
<211> LENGTH: 18
<212> TYPE: PRT
<213> ORGANISM: Artificial
<220> FEATURE:
<223> OTHER INFORMATION: Synthesized Peptide

<400> SEQUENCE: 95

Cys Asp Ser Cys Val Thr His Tyr Pro Tyr Phe Ile Asn Thr Pro Tyr
1               5                   10                  15

Lys Tyr

<210> SEQ ID NO 96
<211> LENGTH: 18
<212> TYPE: PRT
<213> ORGANISM: Artificial
<220> FEATURE:
<223> OTHER INFORMATION: Synthesized Peptide

<400> SEQUENCE: 96

Cys Ala Lys Pro Lys Gln His Tyr Pro Tyr Phe Ile Cys Tyr Pro His
1               5                   10                  15

Glu Cys

<210> SEQ ID NO 97
<211> LENGTH: 16
<212> TYPE: PRT
<213> ORGANISM: Artificial
<220> FEATURE:
<223> OTHER INFORMATION: Synthesized Peptide

<400> SEQUENCE: 97

Ile Asn Lys Thr Gln His Tyr Pro Tyr Phe Ile Glu Tyr Pro Phe His
1               5                   10                  15

<210> SEQ ID NO 98
<211> LENGTH: 18
<212> TYPE: PRT
<213> ORGANISM: Artificial
<220> FEATURE:
<223> OTHER INFORMATION: Synthesized Peptide

<400> SEQUENCE: 98

Cys Pro Asn Thr Gln His His Tyr Pro Tyr Phe Ile Lys Val Gly Glu
1               5                   10                  15

His Cys

<210> SEQ ID NO 99
<211> LENGTH: 18
<212> TYPE: PRT
<213> ORGANISM: Artificial
<220> FEATURE:
<223> OTHER INFORMATION: Synthesized Peptide

<400> SEQUENCE: 99

Cys Pro Asp Ile Ala His His Tyr Pro Tyr Phe Ile Asp Ser Lys Ser
1               5                   10                  15

His Cys

<210> SEQ ID NO 100
<211> LENGTH: 18
<212> TYPE: PRT
<213> ORGANISM: Artificial
<220> FEATURE:
<223> OTHER INFORMATION: Synthesized Peptide

<400> SEQUENCE: 100

Cys Gln Pro Thr Arg His His Tyr Pro Tyr Phe Ile Asp Val Thr Gly
1               5                   10                  15

Arg Cys

<210> SEQ ID NO 101
<211> LENGTH: 18
<212> TYPE: PRT
<213> ORGANISM: Artificial
<220> FEATURE:
<223> OTHER INFORMATION: Synthesized Peptide

<400> SEQUENCE: 101

Cys Gln Asn Asn His His His Tyr Pro Tyr Phe Ile Thr Pro Thr His
1               5                   10                  15

Val Cys

<210> SEQ ID NO 102
<211> LENGTH: 18
<212> TYPE: PRT
<213> ORGANISM: Artificial

```
<220> FEATURE:
<223> OTHER INFORMATION: Synthesized Peptide

<400> SEQUENCE: 102

Cys Thr Thr Thr His Glu His Tyr Pro Tyr Phe Ile Asp Pro Arg Glu
1               5                   10                  15

Ala Cys

<210> SEQ ID NO 103
<211> LENGTH: 18
<212> TYPE: PRT
<213> ORGANISM: Artificial
<220> FEATURE:
<223> OTHER INFORMATION: Synthesized Peptide

<400> SEQUENCE: 103

Cys Thr Thr Pro Ser Arg His Tyr Pro Tyr Phe Ile Asp Gln Leu Gly
1               5                   10                  15

His Cys

<210> SEQ ID NO 104
<211> LENGTH: 18
<212> TYPE: PRT
<213> ORGANISM: Artificial
<220> FEATURE:
<223> OTHER INFORMATION: Synthesized Peptide

<400> SEQUENCE: 104

Cys Asn Ala Asn His Thr His Tyr Pro Tyr Phe Ile Asp Ile Ser Arg
1               5                   10                  15

Lys Cys

<210> SEQ ID NO 105
<211> LENGTH: 16
<212> TYPE: PRT
<213> ORGANISM: Artificial
<220> FEATURE:
<223> OTHER INFORMATION: Synthesized Peptide

<400> SEQUENCE: 105

Gln Phe Thr His Lys His Tyr Pro Tyr Phe Ile Asn Ile Ser Pro Gly
1               5                   10                  15

<210> SEQ ID NO 106
<211> LENGTH: 18
<212> TYPE: PRT
<213> ORGANISM: Artificial
<220> FEATURE:
<223> OTHER INFORMATION: Synthesized Peptide

<400> SEQUENCE: 106

Cys Asn Met Pro His Ser His Tyr Pro Tyr Phe Ile Asn Pro His Gln
1               5                   10                  15

Ser Cys

<210> SEQ ID NO 107
<211> LENGTH: 9
<212> TYPE: PRT
<213> ORGANISM: Artificial
<220> FEATURE:
<223> OTHER INFORMATION: Synthesized Peptide
<220> FEATURE:
<221> NAME/KEY: MOD_RES
<222> LOCATION: (1)..(1)
<223> OTHER INFORMATION: wherein amino acid may be modified with a
```

```
                        7-methoxycoumarin-4-acetyl group
<220> FEATURE:
<221> NAME/KEY: MOD_RES
<222> LOCATION: (9)..(9)
<223> OTHER INFORMATION: Wherein amino acid 9 may be modified with a
                        carboxylated dinitrophenyl group

<400> SEQUENCE: 107

Glu Val Asn Leu Asp Ala Glu Phe Lys
1               5

<210> SEQ ID NO 108
<211> LENGTH: 6
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (6)..(6)
<223> OTHER INFORMATION: wherein amino acid 6 ends with a p-benzoyl
                        phenylalanine-2,3
                        dipropionic acid to which an Alexa488 is bound

<400> SEQUENCE: 108

Tyr Pro Tyr Phe Ile Pro
1               5

<210> SEQ ID NO 109
<211> LENGTH: 6
<212> TYPE: PRT
<213> ORGANISM: Artificial
<220> FEATURE:
<223> OTHER INFORMATION: Synthesized peptide
<220> FEATURE:
<221> NAME/KEY: MOD_RES
<222> LOCATION: (2)..(3)
<223> OTHER INFORMATION: wherein Pro 2 and Phe 3 are joined by a
                        p-benzoyl phenylalanine
<220> FEATURE:
<221> NAME/KEY: MOD_RES
<222> LOCATION: (6)..(6)
<223> OTHER INFORMATION: wherein amino acid 6 ends with a 2,3
                        dipropionic acid to which an
                        Alexa488 is bound

<400> SEQUENCE: 109

Tyr Pro Phe Ile Pro Leu
1               5
```